United States Patent
McGinley et al.

(10) Patent No.: US 12,232,745 B2
(45) Date of Patent: *Feb. 25, 2025

(54) SURGICAL SAW WITH SENSING TECHNOLOGY FOR DETERMINING CUT THROUGH OF BONE AND DEPTH OF THE SAW BLADE DURING SURGERY

(71) Applicant: McGinley Engineered Solutions, LLC, Casper, WY (US)

(72) Inventors: Joseph C. McGinley, Casper, WY (US); Lawson Fisher, Palo Alto, CA (US); Devjeet Mishra, Palo Alto, CA (US); Jim McCrea, Palo Alto, CA (US); Brian Bliven, Palo Alto, CA (US); Martin Leugers, Palo Alto, CA (US)

(73) Assignee: McGinley Engineered Solutions, LLC, Casper, WY (US)

(*) Notice: Subject to any disclaimer, the term of this patent is extended or adjusted under 35 U.S.C. 154(b) by 348 days.

This patent is subject to a terminal disclaimer.

(21) Appl. No.: 17/682,354

(22) Filed: Feb. 28, 2022

(65) Prior Publication Data

US 2022/0175395 A1 Jun. 9, 2022

Related U.S. Application Data

(63) Continuation of application No. 16/433,056, filed on Jun. 6, 2019, now Pat. No. 11,284,906, which is a (Continued)

(51) Int. Cl.
*A61B 17/14* (2006.01)
*A61B 17/15* (2006.01)
(Continued)

(52) U.S. Cl.
CPC ............ *A61B 17/142* (2016.11); *A61B 17/15* (2013.01); *A61B 17/1615* (2013.01);
(Continued)

(58) Field of Classification Search
CPC .............................. A61B 17/14; A61B 17/142
See application file for complete search history.

(56) References Cited

U.S. PATENT DOCUMENTS

| 502,798 A | 8/1893 | Wilbur |
| 1,831,813 A | 11/1931 | Axel |

(Continued)

FOREIGN PATENT DOCUMENTS

| DE | 102011056927 A1 | 6/2013 |
| EP | 3199112 A1 | 8/2017 |

(Continued)

*Primary Examiner* — Andrew Yang
(74) *Attorney, Agent, or Firm* — HOLZER PATEL DRENNAN

(57) ABSTRACT

Sensing technology methods related thereto for determining cut through of bone and a depth of penetration of a working portion of a surgical instrument (e.g., an oscillating saw blade in a cut). A first sensor outputs a first signal representative of a displacement of the cutting edge of the saw blade in the cut. A second sensor outputs a second signal representative of a force applied to the cutting edge of the saw blade. As such, monitoring the first and/or second sensor may allow for the saw to be stopped upon completion of a cut (e.g., when the saw passes completely through a medium to be cut or upon reaching a predetermined depth for the cut).

23 Claims, 26 Drawing Sheets

Related U.S. Application Data continuation of application No. 15/274,475, filed on Sep. 23, 2016, now Pat. No. 10,349,952, which is a continuation of application No. 14/614,125, filed on Feb. 4, 2015, now Pat. No. 9,554,807, which is a continuation of application No. 14/537,586, filed on Nov. 10, 2014, now Pat. No. 9,833,244.

(60) Provisional application No. 61/902,002, filed on Nov. 8, 2013.

(51) Int. Cl.

| | | |
|---|---|---|
| *A61B 17/16* | (2006.01) | |
| *A61B 17/32* | (2006.01) | |
| *A61B 17/3213* | (2006.01) | |
| *A61L 2/07* | (2006.01) | |
| *B08B 3/04* | (2006.01) | |
| *B08B 3/08* | (2006.01) | |
| *A61B 17/00* | (2006.01) | |
| *A61B 17/3207* | (2006.01) | |
| *A61B 90/00* | (2016.01) | |

(52) U.S. Cl.
CPC .. *A61B 17/320068* (2013.01); *A61B 17/3213* (2013.01); *A61L 2/07* (2013.01); *B08B 3/04* (2013.01); *B08B 3/08* (2013.01); *A61B 2017/00017* (2013.01); *A61B 2017/00022* (2013.01); *A61B 2017/00075* (2013.01); *A61B 17/149* (2016.11); *A61B 17/320758* (2013.01); *A61B 2090/061* (2016.02); *A61B 2090/062* (2016.02); *A61B 2090/064* (2016.02); *A61B 2090/0812* (2016.02); *A61B 2090/0813* (2016.02); *A61B 2090/0814* (2016.02)

(56) References Cited

U.S. PATENT DOCUMENTS

| | | | |
|---|---|---|---|
| 2,883,891 | A | 4/1959 | Shulters et al. |
| 3,804,544 | A | 4/1974 | Adams |
| 4,014,621 | A | 3/1977 | Johnson et al. |
| 4,063,356 | A * | 12/1977 | Hepworth ............... B26B 5/002 30/162 |
| 4,157,231 | A | 6/1979 | Phillips |
| 4,310,269 | A | 1/1982 | Neu et al. |
| 4,329,092 | A | 5/1982 | Poenitzsch et al. |
| 4,329,095 | A | 5/1982 | Schmuck |
| 4,644,335 | A | 2/1987 | Wen |
| 4,710,075 | A | 12/1987 | Davison |
| 4,723,911 | A | 2/1988 | Kurtz |
| 4,765,333 | A | 8/1988 | Bray |
| 4,867,158 | A | 9/1989 | Sugg |
| 4,951,690 | A | 8/1990 | Baker |
| 5,013,194 | A | 5/1991 | Wienhold |
| 5,014,793 | A | 5/1991 | Germanton et al. |
| 5,022,798 | A | 6/1991 | Eckman |
| 5,071,293 | A | 12/1991 | Wells |
| 5,133,728 | A | 7/1992 | Petersen |
| 5,139,376 | A | 8/1992 | Pumphrey |
| 5,161,921 | A | 11/1992 | Corsi |
| 5,277,799 | A | 1/1994 | Bransch |
| 5,361,504 | A | 11/1994 | Huang |
| 5,380,333 | A | 1/1995 | Meloul et al. |
| 5,411,503 | A | 5/1995 | Hollstien et al. |
| 5,533,842 | A | 7/1996 | Johnson et al. |
| 5,538,423 | A | 7/1996 | Coss et al. |
| 5,584,838 | A | 12/1996 | Rona et al. |
| 5,599,142 | A | 2/1997 | Fujimoto et al. |
| 5,613,810 | A | 3/1997 | Bureller |
| 5,810,828 | A | 9/1998 | Lightman et al. |
| 5,957,947 | A * | 9/1999 | Wattiez ............... A61B 17/3417 606/185 |
| 5,961,257 | A | 10/1999 | Bettini et al. |
| 5,980,248 | A | 11/1999 | Kusakabe et al. |
| 6,033,409 | A | 3/2000 | Allotta |
| 6,081,741 | A | 6/2000 | Hollis |
| 6,096,042 | A | 8/2000 | Herbert |
| 6,342,057 | B1 | 1/2002 | Brace et al. |
| 6,494,590 | B1 | 12/2002 | Paganini et al. |
| 6,527,778 | B2 | 3/2003 | Athanasiou et al. |
| 6,587,184 | B2 | 7/2003 | Wuersch et al. |
| 6,665,948 | B1 | 12/2003 | Kozin et al. |
| 6,786,683 | B2 | 9/2004 | Schaer et al. |
| 6,925,725 | B2 | 8/2005 | Herrmann et al. |
| 7,073,989 | B2 | 7/2006 | Erickson et al. |
| 7,185,998 | B2 | 3/2007 | Oomori et al. |
| 7,220,088 | B2 | 5/2007 | Ferrari et al. |
| 7,235,940 | B2 | 6/2007 | Bosch et al. |
| 7,314,048 | B2 | 1/2008 | Couture et al. |
| 7,482,819 | B2 | 1/2009 | Wuersch |
| 7,578,642 | B2 | 8/2009 | Fritsche et al. |
| 7,681,659 | B2 | 3/2010 | Zhang et al. |
| 7,691,106 | B2 | 4/2010 | Schenberger et al. |
| 7,840,253 | B2 | 11/2010 | Tremblay et al. |
| 7,946,049 | B1 | 5/2011 | Wilton |
| 7,992,311 | B2 | 8/2011 | Cerwin |
| 8,092,457 | B2 | 1/2012 | Oettinger et al. |
| 8,162,074 | B2 | 4/2012 | Cook |
| 8,167,518 | B2 | 5/2012 | Mathis et al. |
| 8,171,642 | B2 | 5/2012 | Fritsche et al. |
| 8,317,437 | B2 | 11/2012 | Merkley et al. |
| 8,460,297 | B2 | 6/2013 | Watlington et al. |
| 8,463,421 | B2 | 6/2013 | Brett et al. |
| 8,511,945 | B2 | 8/2013 | Apkarian et al. |
| 8,734,153 | B2 | 5/2014 | Arzanpour et al. |
| 8,894,654 | B2 | 11/2014 | Anderson |
| 8,925,169 | B2 | 1/2015 | Schevers |
| 8,970,207 | B2 | 3/2015 | Baumgartner |
| 9,022,949 | B2 | 5/2015 | Herndon |
| 9,114,494 | B1 | 8/2015 | Mah |
| 9,204,885 | B2 | 12/2015 | McGinley et al. |
| 9,358,016 | B2 | 6/2016 | McGinley et al. |
| 9,370,372 | B2 | 6/2016 | McGinley et al. |
| 9,492,181 | B2 | 11/2016 | McGinley et al. |
| 9,821,493 | B2 | 11/2017 | Anderson et al. |
| 9,826,984 | B2 | 11/2017 | McGinley et al. |
| 9,855,060 | B2 | 1/2018 | Ardel |
| 2001/0031919 | A1 | 10/2001 | Strommer et al. |
| 2001/0047219 | A1 | 11/2001 | Oden |
| 2002/0165549 | A1 | 11/2002 | Owusu-Akyaw et al. |
| 2003/0049082 | A1 | 3/2003 | Morrison et al. |
| 2003/0229351 | A1 | 12/2003 | Tidwell et al. |
| 2004/0146367 | A1 | 7/2004 | Gerhardt et al. |
| 2004/0179829 | A1 | 9/2004 | Phillips et al. |
| 2004/0215395 | A1 | 10/2004 | Strasser et al. |
| 2005/0116673 | A1 | 6/2005 | Carl et al. |
| 2005/0131415 | A1 | 6/2005 | Hearn et al. |
| 2005/0169717 | A1 | 8/2005 | Field |
| 2005/0261870 | A1 | 11/2005 | Cramer et al. |
| 2006/0004371 | A1 | 1/2006 | Williams et al. |
| 2006/0008771 | A1 | 1/2006 | Courvoisier |
| 2006/0025677 | A1 | 2/2006 | Verard et al. |
| 2006/0074292 | A1 | 4/2006 | Thomson et al. |
| 2006/0241628 | A1 | 10/2006 | Parak |
| 2006/0258938 | A1 | 11/2006 | Hoffman et al. |
| 2007/0030486 | A1 | 2/2007 | Gelbart |
| 2007/0035311 | A1 | 2/2007 | Wuersch |
| 2007/0041799 | A1 | 2/2007 | Schaefer et al. |
| 2008/0119725 | A1 | 5/2008 | Lloyd |
| 2008/0167653 | A1 | 7/2008 | Watlington et al. |
| 2008/0226409 | A1 | 9/2008 | Hasenzahl |
| 2008/0228195 | A1 | 9/2008 | Von et al. |
| 2008/0243125 | A1 | 10/2008 | Guzman et al. |
| 2008/0292416 | A1 | 11/2008 | Kado et al. |
| 2009/0131986 | A1 | 5/2009 | Lee et al. |
| 2009/0182226 | A1 | 7/2009 | Weitzner et al. |
| 2009/0245956 | A1 | 10/2009 | Apkarian et al. |
| 2009/0299439 | A1 | 12/2009 | Saladino et al. |
| 2009/0326537 | A1 | 12/2009 | Anderson |
| 2010/0114099 | A1 | 5/2010 | Patwardhan |
| 2010/0137874 | A1 | 6/2010 | Kim et al. |
| 2010/0239380 | A1 | 9/2010 | Amirov et al. |

(56) References Cited

U.S. PATENT DOCUMENTS

| | | |
|---|---|---|
| 2011/0020084 A1 | 1/2011 | Brett et al. |
| 2011/0060242 A1 | 3/2011 | Mrva et al. |
| 2011/0245831 A1 | 10/2011 | Giersch et al. |
| 2011/0245832 A1 | 10/2011 | Giersch et al. |
| 2011/0245833 A1 | 10/2011 | Anderson |
| 2011/0301611 A1 | 12/2011 | Garcia et al. |
| 2012/0123418 A1 | 5/2012 | Giurgi et al. |
| 2012/0179070 A1 | 7/2012 | Pommer et al. |
| 2012/0253348 A1 | 10/2012 | Arlettaz et al. |
| 2013/0122466 A1 | 5/2013 | Connor et al. |
| 2013/0237811 A1 | 9/2013 | Mihailescu et al. |
| 2013/0304069 A1 | 11/2013 | Bono et al. |
| 2013/0307529 A1 | 11/2013 | Baumgartner |
| 2013/0327552 A1 | 12/2013 | Lovelass et al. |
| 2014/0039517 A1 | 2/2014 | Bowling et al. |
| 2014/0081659 A1 | 3/2014 | Nawana et al. |
| 2014/0107471 A1 | 4/2014 | Haider et al. |
| 2014/0275760 A1 | 9/2014 | Lee et al. |
| 2014/0275989 A1 | 9/2014 | Jacobsen et al. |
| 2014/0350685 A1 | 11/2014 | Bagga et al. |
| 2015/0066030 A1 | 3/2015 | McGinley et al. |
| 2015/0066035 A1 | 3/2015 | McGinley et al. |
| 2015/0066036 A1 | 3/2015 | McGinley et al. |
| 2015/0066037 A1 | 3/2015 | McGinley et al. |
| 2015/0066038 A1 | 3/2015 | McGinley et al. |
| 2015/0165580 A1 | 6/2015 | Holland |
| 2016/0120553 A1 | 5/2016 | Xie |
| 2016/0178343 A1 | 6/2016 | Hale et al. |
| 2016/0247276 A1 | 8/2016 | Chou et al. |
| 2017/0128081 A1 | 5/2017 | McGinley |
| 2017/0143396 A1 | 5/2017 | McGinley et al. |
| 2017/0245868 A1 | 8/2017 | McGinley et al. |
| 2017/0345398 A1 | 11/2017 | Fuchs et al. |
| 2018/0070113 A1 | 3/2018 | Phillips et al. |
| 2018/0110572 A1 | 4/2018 | Flatt |
| 2018/0260931 A1 | 9/2018 | Ozguner et al. |
| 2019/0209287 A1 | 7/2019 | Zenz-Olson |

FOREIGN PATENT DOCUMENTS

| | | |
|---|---|---|
| WO | 9724991 A1 | 7/1997 |
| WO | 2015006296 A1 | 1/2015 |
| WO | 2015014771 A2 | 2/2015 |
| WO | 2015034562 A1 | 3/2015 |
| WO | 2015082904 A1 | 6/2015 |
| WO | 2016207628 A1 | 12/2016 |

* cited by examiner

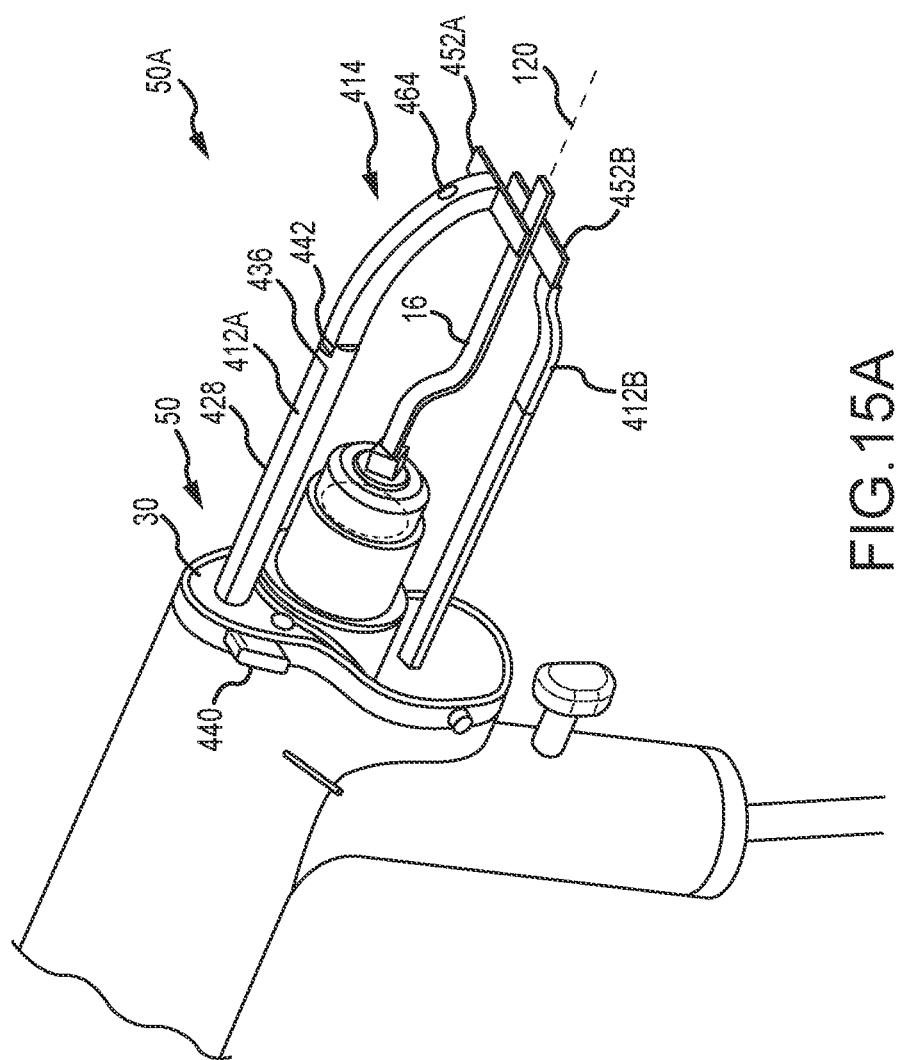

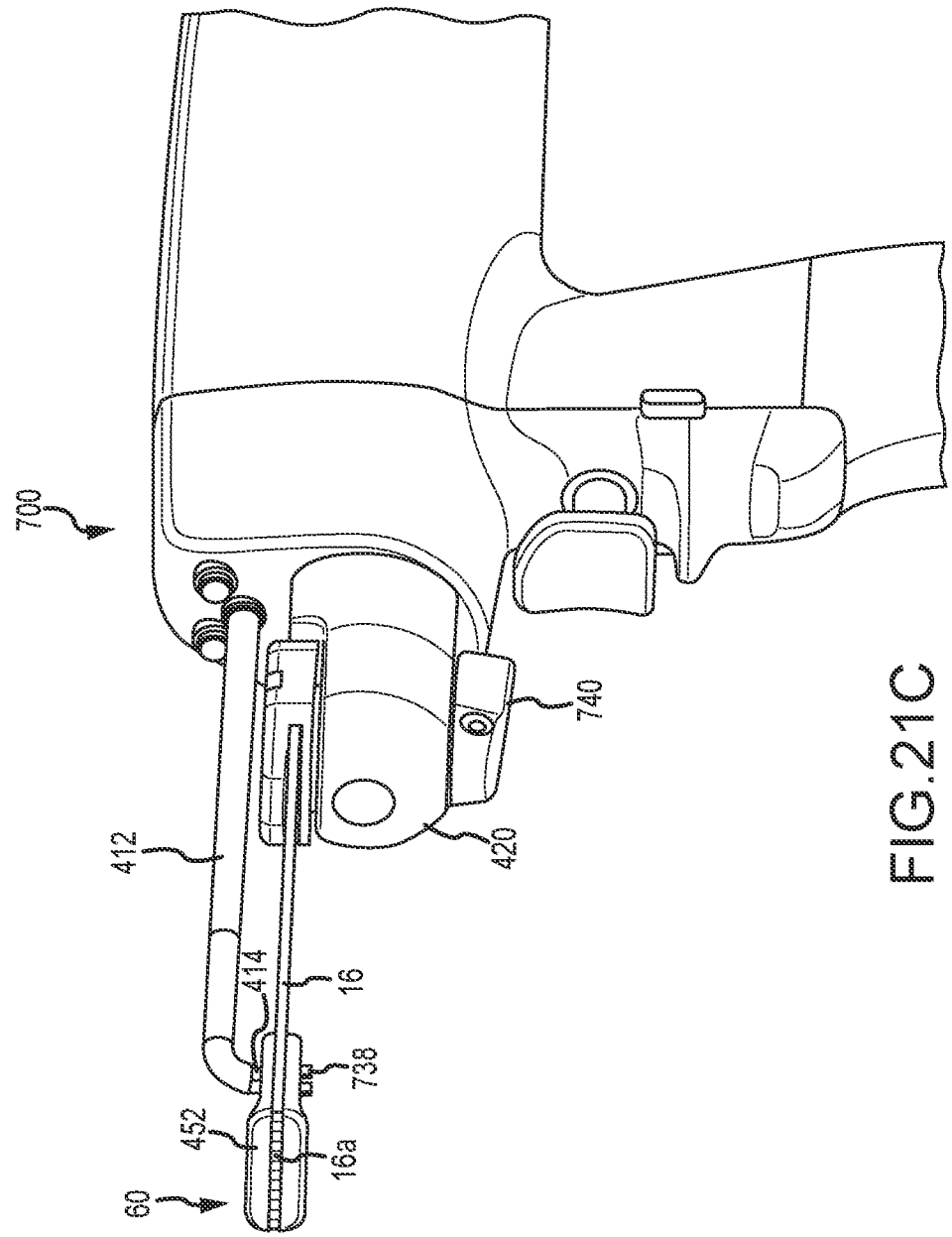

SURGICAL SAW WITH SENSING TECHNOLOGY FOR DETERMINING CUT THROUGH OF BONE AND DEPTH OF THE SAW BLADE DURING SURGERY

RELATED APPLICATIONS

This application is a continuation of U.S. application Ser. No. 16/433,056, filed on Jun. 6, 2019, entitled "SURGICAL SAW WITH SENSING TECHNOLOGY FOR DETERMINING CUT THROUGH OF BONE AND DEPTH OF THE SAW BLADE DURING SURGERY," which is a continuation of U.S. Non-Provisional application Ser. No. 15/274,475 filed Sep. 23, 2016, entitled "SURGICAL SAW WITH SENSING TECHNOLOGY FOR DETERMINING CUT THROUGH OF BONE AND DEPTH OF THE SAW BLADE DURING SURGERY," which is a continuation of U.S. Non-Provisional application Ser. No. 14/537,586 filed Nov. 10, 2014, entitled "SURGICAL SAW WITH SENSING TECHNOLOGY FOR DETERMINING CUT THROUGH OF BONE AND DEPTH OF THE SAW BLADE DURING SURGERY," which claims the benefit of U.S. Provisional Application No. 61/902,002 filed Nov. 8, 2013, entitled "SURGICAL SAW WITH SENSING TECHNOLOGY FOR DETERMINING CUT THROUGH OF BONE AND DEPTH OF THE SAW BLADE DURING SURGERY," the contents of which are incorporated by reference herein as if set forth in full.

BACKGROUND

Orthopedic sawing procedures may result in incorrect saw lengths or damage to a patient (i.e., if the sawing action continues after cut completion or if an incorrect cut depth is made), which can lead to surgical complications. Furthermore, in cases where the length of a cut made using a surgical saw is to be determined, determining the length for a cut can be a time consuming procedure which is undesirable when tissue is exposed and potentially subjected to infection.

As shown in FIG. 1, a cross section of a bone 10 having with a hard cortex 12 is shown. The bone 10 may be surrounded by a medium 14 that is less dense than the hard cortex 12 (e.g., soft tissue or air in the case of a bone exposed during a surgical procedure). In orthopedic procedures, it may be necessary to saw a bone 10 (e.g., saw a portion of a bone or completely through a bone). When cutting through all or a portion of a bone 10, failure to arrest oscillation of the saw blade as soon as a cut is complete may result in unnecessary damage to the area around the cut. Furthermore, precise control over the depth of a cut may be needed in certain surgical operations.

Previously proposed techniques for sawing include the surgeon making a cut through the bone until the surgeon "feels" the saw blade pass completely through the bony structure or have the surgeon estimate a depth of the cut during the cutting operation. That is, the surgeon must rely on his or her senses and judgment alone to determine when the saw blade has passed completely through the bony structure or to a predetermined depth. Once the surgeon believes that he or she has passed completely through the structure or to the predetermined depth, the saw blade oscillation is arrested by the surgeon. Thereafter the surgeon may measure the length of the cut. A possible resulting complication of this procedure is that the surgeon may mistakenly "feel" the saw blade pass through a layer of differing density, thus falsely believing the cut to be complete. Additionally, the surgeon may not precisely "feel" the saw blade pass through the bone, thereby possibly damaging tissue on the opposite side of the bone.

Additionally, it may be necessary of a surgeon to measure the cut length once the cut is complete or stop cutting at a prescribed length that was predetermined by imaging software or a measurement jig. However, access to the anatomy that is cut may be limited, thus also limiting the ability to use such measurement jigs or other fixtures to control the depth of a cut. As such, traditional measurement techniques for verification of the cut length may be subject to error. As such, the process of sawing to a measured depth often includes inaccurate guess work. Conservative sawing may result in incomplete sawing (i.e., failure to saw completely through the bone or failure to saw to a predetermined depth), thus requiring multiple attempts. As such, sawing to a predefined depth is quite difficult. Additionally, it may be difficult to quickly arrest the saw blade motion upon cut completion. As such, the process may consume a substantial amount of surgical time resulting in a large cost per patient. By combining the sawing and depth measurement process into one accurate procedure, cost is reduced along with a decrease in patient morbidity.

SUMMARY

The present disclosure relates generally to systems, methods, and apparatuses for use in connection with determining when an instrument working portion (e.g., a cutting edge of a surgical saw) has completed a desired cut (i.e., has completed a cut of a certain length that may correspond to completely through a bone or partially through a bone). More specifically, the present disclosure presents embodiments related to a system and method for determining the length of a cut made through a bone of a patient without removing the saw blade from the cut formed in the bone. As such, in at least some embodiments herein, a saw is disclosed that automatically cease a cutting operation upon passing completely through a bone. Also, embodiments of a saw that automatically arrests a sawing action upon achieving a predetermined depth of cut are described. The present disclosure may thus include embodiments that allow for a saw blade to cut through a bone to a predetermined depth (e.g. measured from a portion of the bone or a cutting guide). Accordingly, the present disclosure may find application in the field of surgical sawing where the depth of the cut made in a bone is to be determined.

The present disclosure also includes embodiments of saw blade assemblies that may be specifically adapted for use for saw blade penetration measurement. Accordingly, the saw blade assemblies and saws disclosed herein may provide increased efficiency, reliability, and accuracy in relation to a saw blade penetration measurement system. For instance, in certain embodiments, a saw blade assembly may be used in conjunction with a saw as described herein to provide an improved platform to facilitate measurement of a cut created by the saw using a saw blade penetration measurement system without having to remove the saw blade from the cut during operation.

Systems for drill bit penetration measurement systems have been proposed such as described in U.S. Pat. No. 6,665,948, the entirety of which is incorporated herein by reference. In this regard, the description presented herein may provide adaptations, refinements, and/or additional features for use in connection with a saw blade penetration measurement system. As such, the present disclosure may facilitate improvements in the efficiency, accuracy, and or ergonomics of prior approaches to surgical saws.

Accordingly, a first aspect includes a saw blade assembly for use with a saw having a displacement sensor for outputting a signal representative of a displacement of the saw blade with respect to a reference point. The assembly includes a saw blade, a bushing, and an engagement member disposed on the bushing. The saw blade may include a cutting edge disposed at a distal end of the saw blade. Alternatively, the saw blade may include a cutting edge that extends along a length of the saw blade (e.g., along a majority or substantially all of the saw blade). The saw blade may include a shank that is adapted for engagement with a drive assembly that provides an oscillating motion of the saw blade during operation. The bushing may engage at least a portion of the saw blade or shank (e.g., through an aperture in the bushing or the saw blade). As such, the bushing may be constrainedly moveable relative to the blade or shank in a direction along a cutting direction of the saw blade. The engagement member is adapted for engagement with a displacement sensing arm of the displacement sensor. In this regard, the engagement member is engageable with the displacement sensing arm for corresponding movement between the bushing and the displacement sensing arm.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, in an embodiment, an aperture may be provided at the bushing that may define an opening extending from a distal end of the bushing to a proximal end of the bushing. In this case, the distal end of the opening may comprise a reference surface. The reference surface may extend at least partially along a portion of the saw blade when disposed in the aperture. In other embodiments, the bushing may be conformably shaped relative to the body of the saw blade to facilitate the constrained movement relative to the oscillation of the blade. In such embodiments, the bushing may or may not extend about entirety of the shank. For example, the bushing may include a dished or concave surface that is alignable with the body or shank of the saw blade for constrained movement in a direction along the sawing axis. In any regard, the saw blade may be moved relative to the reference surface when making a cut in a medium so that the displacement between the saw blade and the bushing may be measured.

In any regard, the bushing may be disposable adjacent to the cutting edge of the saw blade (i.e., adjacent to the distal end of the saw blade). Accordingly, the reference surface may be alignable with the cutting edge of the saw blade to define a reference point from which displacement of the saw blade may be measured when making a cut using the saw blade. In this regard, the displacement sensing arm to which the bushing is engageable may be operatively engaged with a displacement sensor of a saw as will be described in greater detail below. In this regard, the saw blade may be advanceable relative to a medium to be cut to create a cut such that the cutting edge of the saw blade is displaced relative to the reference surface upon the advancement of the saw blade into the cut. Accordingly, when the engagement member operatively engages a displacement sensing arm of a displacement sensor, the displacement sensor may measure the displacement of the cutting edge from the reference surface.

In an embodiment, the reference surface may contact a peripheral portion extending about the cut (e.g., on at least a first side of the cut) upon advancement of the saw blade to create the cut. The bushing may be engageable against the peripheral portion extending about the cut so as to maintain the reference point stationary against the peripheral portion of the cut in a cutting direction. For instance, the bushing may be biased toward the distal end of the saw blade (e.g., under the influence of the displacement sensing arm or by another biasing member disposed relative to the saw blade and the bushing). In this regard, as the reference surface of the bushing may be maintained adjacent to the surface to be sawed, the accuracy of the displacement measure upon advancement of the saw blade may be improved given the proximity of contact of the bushing defining the reference surface relative to the location of the cut.

In various embodiments, the engagement member may include any appropriate mechanism for attachably connecting the bushing to a displacement sensing arm. In one particular embodiment, the engagement member may include a post extending from the bushing that is selectively engageable with the displacement sensing arm of the displacement sensor. In this regard, the post may facilitate relative pivotal movement between the post of the bushing and the displacement sensing arm (e.g., prior to engagement of the shank with the saw). Further still, the bushing may include a snap interface that engages the displacement sensing arm. As such, the snap interface may include fingers that snappingly engage the displacement sensing arm (e.g., at a configured distal portion thereof that is shaped to correspond to the fingers of the bushing). That is, the bushing may be snapped to a portion of the displacement sensing arm. In any regard, movement that engages the bushing with the displacement sensing arm may allow for improved ergonomics when engaging the saw blade assembly with a saw by allowing the shank to be aligned with the saw after engagement of the bushing with the displacement sensing arm.

In another embodiment, the saw may not include a bushing, but the blade or saw is received, guided or supported by a cutting guide or jig. The cutting guide or jig guides the saw blade or the saw along a sawing axis. A displacement sensor using the cutting guide or jig as a reference surface for measuring cutting depth may be provided where the displacement sensor may be in contact with a stationary portion of the cutting guide as the saw blade is advanced through the bone to determine the depth of a cut made.

In an embodiment, the saw blade assembly may be provided as a one-time use, disposable component for use in a surgery or other operation. In this regard, the saw blade assembly may include features that help reduce the likelihood that the saw blade is reused in contradiction of instructions regarding one time use. Such features may at least reduce the functionality of the saw blade assembly (e.g., potentially to the point where the saw blade assembly is incapable of reuse with the measurement system). For example, in an embodiment, the shank may include a destructible portion that is at least partially destructible during a cleaning process. Additionally or alternatively, the bushing (e.g., the engagement portion of the bushing) may comprise a destructible portion that, when destroyed, limits or prevents reuse with the measurement system. In this regard, the bushing or a portion thereof (e.g., an engagement portion) may be destroyed during a cleaning process to avoid reuse of the blade after cleaning. In one particular embodiment, the destructible portion may be meltable. As such, a melting temperature of the destructible portion may be greater than an operating temperature of the saw blade and less than an autoclave temperature. As such, the destructible portion may remain intact during operation of the saw blade assembly. However, upon undergoing a cleaning or sterilization process (e.g., autoclaving), the destructible portion may be at least partially degraded. In one embodiment, the melting temperature of the destructible portion is not less than about 60° C. and not greater than about 110° C. The destructible portion may also be destroyed upon exposure to a cleaning or sanitizing chemical or the like used in the cleaning process (e.g., as an alternative to or in addition to being meltable).

In view of the foregoing, the destruction of the destructible portion may alter the shape of the shank of the saw blade or the bushing such that engagement with a saw or a measurement system thereof may be at least partially prevented or degraded. For instance, the destructible portion may be used to at least partially establish registration between the shank and a chuck of the saw. Accordingly, upon destruction of the destructible portion, registration between the saw blade assembly and the chuck of the saw may be reduced (e.g., potentially to the point of inoperability of the saw blade). For example, the destructible portion may include a proximal end portion of the shank. In this regard, the destructible portion may include at least a portion of an engagement feature for engagement of the shank by the chuck. In an embodiment, the destructible portion may include at least a portion of at least one sidewall of the shank. Additionally or alternatively, the engagement feature may include a detent engageable by an engagement member in the chuck. As such, the destructible portion, after having been exposed to a cleaning process, may not be registerable with respect to assembly chuck of the saw. That is, the surface area of the engagement feature of the shank that is in contact with the chuck when the saw blade is engaged with the chuck may be at least reduced upon exposure of the destructible portion to a cleaning process. Further still, as the destructible portion may comprise at least a portion of the bushing, the bushing may be degraded in a cleaning process such that destruction of the destructible portion results in the bushing not being engageable with the displacement sensing arm.

A second aspect includes a method for use of a saw blade assembly with a saw having a displacement sensor for outputting a signal representative of a displacement of a cutting edge of the saw blade assembly with respect to a reference point. The method may include engaging a displacement sensing arm of the displacement sensor with an engagement member of a bushing. The bushing may be constrainedly moveable relative to a saw blade along a cutting direction of the saw blade during sawing. The engaging may result in corresponding movement of the bushing and the displacement sensing arm. The method may include aligning a shank of the saw blade with a chuck of the saw and securing the shank with the chuck of the saw to restrict movement between the saw blade and the motor assembly.

A number of feature refinements and additional features are applicable to the second aspect. These feature refinements and additional features may be used individually or in any combination. As such, each of the following features that will be discussed may be, but are not required to be, used with any other feature or combination of features of the second aspect. For example, in an embodiment, the saw blade assembly may be provided in accord with any of the features and/or feature refinements described above in connection with the first aspect.

For example, in an embodiment, the method may include positioning a distal portion of the bushing adjacent to a cutting edge of the saw blade (e.g., at a distal portion thereof). In this regard, the method may also include contacting the cutting edge of the saw blade to a surface of a medium to be sawed. Accordingly, the distal portion of the bushing may contact the surface of the medium to be sawed. As such, the method may also include establishing the reference point when the cutting edge of the saw blade and the distal portion of the bushing are in contact with the surface of the medium to be sawed. The method may also include advancing the saw blade into the medium to be sawed, such that the cutting edge advances in relation to the distal portion of the bushing in contact with the surface of the medium to be sawed. Thus, the method may include producing relative movement of the displacement sensing arm relative to the displacement sensor upon advancing the saw blade into the medium. As the displacement sensing arm may be operatively engaged with the displacement sensor, the method may further include outputting a signal from the displacement sensor indicative of the amount of displacement of the cutting edge of the saw blade relative to the distal portion of the bushing. In other embodiments, the saw may include a displacement sensing arm in direct contact with a medium to be cut or a cutting guide disposed stationary relative to a medium to be cut. In this regard, relative motion between the saw blade and the medium to be cut may be measured by the displacement sensing arm.

A third aspect includes a saw blade assembly for use in a medical saw for single use applications. The saw blade assembly includes a saw blade with a cutting edge and a shank. The assembly also includes a bushing. The saw blade assembly includes a destructible portion. The cutting edge is disposed at a distal end of the saw blade. The shank is disposed adjacent to a proximal end of the saw blade, and a blade body member extends along a length of the saw blade between the distal end and the proximal end. The shank and/or bushing may include the destructible portion that is at least partially destructible during a cleaning process. The bushing may be at least partially captured by the shank such that the bushing is non-removably engaged with the shank when the destructible portion is intact. Upon destruction of the destructible portion, the bushing may no longer be engaged with the shank and/or an engagement portion may be destroyed, thus preventing engagement with the displacement sensing arm upon destruction of the destructible portion.

A number of feature refinements and additional features are applicable to the third aspect. These feature refinements and additional features may be used individually or in any combination. As such, each of the following features that will be discussed may be, but are not required to be, used with any other feature or combination of features of the third aspect or any of the other aspects disclosed herein.

For example, in an embodiment, the destructible portion may be meltable. In this regard, a melting temperature of the destructible portion may be greater than an operating temperature of the saw blade and less than an autoclave temperature. For instance, the melting temperature of the destructible portion may be not less than about 60° C. and not greater than about 110° C. Additionally, as referenced above in connection with the first aspect, the destructible portion may be destroyed upon exposure to a cleaning or sanitizing chemical or the like used during a cleaning and/or sanitizing process.

As described above with respect to the first aspect, the destructible portion may comprise a proximal end portion of the shank. Thus, upon destruction of the destructible portion, at least a portion of the shank may undergo a change in shape. Accordingly, the destructible portion may include at least a portion of an engagement feature for engagement of the shank by a chuck of a saw. For instance, the destructible portion may include at least a portion of at least one sidewall of the shank. Additionally or alternatively, the engagement feature may include a detent engageable by the chuck (e.g., the detent features may correspond with a quick-change style chuck device where the detents are used to selectively retain the shank in the chuck device). Further still, the destructible portion, after destruction thereof, may prevent engagement of the bushing with the displacement sensing arm and/or may destroy engagement between the saw blade and the bushing.

Accordingly, in an embodiment, the destructible portion, after having been exposed to a cleaning process, may not be registerable with respect to the chuck device. In this regard, the surface area of the sidewall of the shank may be at least reduced upon exposure of the destructible portion to a cleaning process (e.g., an autoclave process or a chemical sanitation process).

A fourth aspect includes a method for a saw blade assembly for use in a medical saw for single use applications. The method includes exposing the saw blade assembly to a cleaning process and degrading at least a portion of a destructible portion. For example, the destructible portion may comprise a portion of the shank and/or a portion of a bushing provided with the saw blade assembly. In either case, the destructible portion may be degraded in response to the exposing such that the saw blade assembly is not functional after the degrading. Additionally, a number of feature refinements and additional features are applicable to the fourth aspect. These feature refinements and additional features may be used individually or in any combination. As such, each of the following features that will be discussed may be, but are not required to be, used with any other feature or combination of features of any of the aspects discussed herein.

For instance, in an embodiment the exposing may include autoclaving the saw blade. As such, the degrading may include melting at least a portion of the destructible portion in response to the autoclaving. The melting may occur at a temperature of not less than about 60° C. and not greater than about 110° C. In this regard, the destructible portion may withstand temperatures associated with normal operation of the saw blade, but may be degraded (i.e., melted) upon exposure to the autoclaving process. In another embodiment, the exposing may include applying a cleaning chemical to the saw blade such that the degrading includes removal of at least a portion of the destructible portion in response to applying the cleaning chemical.

As described above, in an embodiment the degrading may result in changing a shape of a shank of the saw blade. Thus, the degrading may include removing at least a portion of the destructible portion at a shank of the saw blade. The portion of the destructible portion removed may at least be a portion of an engagement feature for engagement of the shank by a chuck device of a saw. For instance, the destructible portion may include at least a portion of at least one sidewall of the shank or may include a detent engageable by the chuck device. In any regard, the degrading may result in reducing the registration of the shank with respect to a chuck device of a saw. Additionally or alternatively, a portion (e.g., an engagement portion) of a bushing of the saw blade assembly may comprise the destructible portion that is degraded to prevent the bushing from engaging with a displacement sensing arm.

A fifth aspect includes a saw including a saw blade penetration measuring system for determining, with respect to a reference point, a depth of penetration of a cutting edge of a saw blade in a cut. The saw includes a chuck for engagement with a shank of a saw blade. The chuck is operable to constrain a saw blade engaged by the chuck during sawing. The saw also includes a displacement sensing arm extending from the saw that may be engageable with a bushing member that is constrainedly moveable with respect to a saw blade engaged by the chuck. The saw also includes a displacement sensor disposed in a fixed relative position with respect to a saw blade engaged by the chuck. The displacement sensor is adapted for relative movement with respect to the displacement sensing arm. Accordingly, the displacement sensor is operative to output a first signal representative of the displacement of the sensing arm relative to the displacement sensor. The movement of the displacement sensing arm relative to the saw corresponds to displacement of the bushing relative to a saw blade engaged by the chuck. In this regard, movement of the displacement sensing arm relative to the saw and the corresponding movement of the saw blade relative to the bushing may be measured as an output of the displacement senor of the saw.

A number of feature refinements and additional features are applicable to the fifth aspect. These feature refinements and additional features may be used individually or in any combination. As such, each of the following features that will be discussed may be, but are not required to be, used with any other feature or combination of features of the fifth aspect. Furthermore, any of the features discussed in relation to any other aspect discussed herein may be used with the fifth aspect.

For example, in an embodiment, the displacement sensor may be disposed internally to a saw housing and the displacement sensing arm may extend from the saw housing. Accordingly, the displacement sensing arm may extend from the saw housing. As such, at least a portion of the displacement sensing arm (e.g., a proximal portion thereof) may extend towards a saw blade engaged by the chuck. In an embodiment, the displacement sensing arm may include a hole engageable with a post of the bushing to effectuate corresponding movement of the displacement sensing arm and the bushing. In another embodiment, the bushing may have a snap interface such that a portion of the bushing snaps about a portion of the displacement sensing arm to engage therewith.

In an embodiment, the displacement sensor may include a linear variable differential displacement transducer (LVDT). Accordingly, a coil of the LVDT may be disposed in the housing and the displacement sensing arm may include a moveable core displaceable with respect to the coil of the LVDT. The displacement sensor may have a total measureable travel of at least about 2.5 inches (6.4 cm). However, any other appropriate type of displacement sensor (e.g., a relative or absolute position sensor) may be used such as, for example, an optical sensor or the like. Furthermore, other appropriate types of sensors or sensor systems may be employed including digital encoders, laser sensors, 3D triangulation based on imaging and fiducial markings, etc.

In an embodiment, the displacement sensing arm may be biased to a distal position relative to a saw blade engaged by the chuck. Additionally or alternatively, the displacement sensing arm may be selectively removable from the saw housing. Further still, the displacement sensing arm may be selectively retainable in a proximal position. The displacement sensing arm may be selectively removable from a passage extending through the saw housing, such that the passageway is selectively opened from a proximal end thereof to a distal end thereof (e.g., by removal of the displacement sensing arm and/or removal of an end cap or the like).

In an embodiment, the chuck of the saw may include a removable assembly engaged to a drive motor by way of a coupling receiver. The removable assembly may be attached to the saw by way of a release mechanism. As such, the chuck may be selectively removable from the saw.

In an embodiment, the saw may include a light emitter operable to emit light in a direction toward the saw blade retained by the chuck.

A sixth aspect includes a method for use of a saw including a saw blade penetration measuring system for determining, with respect to a reference point, a depth of penetration of cutting edge of a saw blade in a cut. The method includes engaging a shank of a saw blade with a chuck of the saw. The method also includes constraining the saw blade engaged by the chuck to limit relative axial movement between the saw and saw blade during sawing. The method further includes connecting a displacement sensing arm extending from the saw to a bushing member that is constrainedly moveable with respect to the saw blade engaged with the chuck.

A number of feature refinements and additional features are applicable to the sixth aspect. These feature refinements and additional features may be used individually or in any combination. As such, each of the following features that will be discussed may be, but are not required to be, used with any other feature or combination of features of the sixth aspect. Furthermore, any of the features discussed in relation to any other aspect discussed herein may be used with the sixth aspect.

For example, the method may also include aligning a distal edge of the bushing with a cutting edge of the saw blade and moving the displacement sensing arm relative to a displacement sensor of the saw. However, in other embodiments, the displacement sensing arm may contact a cutting guide to establish a reference point. In any regard, the method may include establishing the reference point relative to the cutting edge of the saw blade. Furthermore, the method may include oscillating the saw blade to create a cut to advance the saw blade in the cut and detecting a relative movement of the saw blade relative to the reference point by way of corresponding movement of the displacement sensing arm relative to the displacement sensor. As such, a displacement may be measured. The saw may be stopped automatically in response to completion of a cut (i.e., sawing through a bone or the like) which may be determined upon monitoring a displacement sensor and/or a force sensor. Furthermore, a predetermined displacement may be set such that the saw may be stopped upon displacement of the saw blade to the predetermined displacement length. The method may include biasing the displacement sensing arm to a distal position, wherein the biasing maintains the distal edge of the bushing in contact with a medium into which the saw blade is advanced to create the cut.

A seventh aspect includes a saw including a saw blade penetration measurement system for determining, with respect to a reference point, a depth of a penetration of a cutting edge of a saw blade in a cut along a cutting axis when the cutting edge of the saw blade passes from a first medium to a second medium, the first medium contiguous with the second medium, the first medium having a first density, the second medium having a second density. The saw includes a first sensor outputting a first signal representative of a displacement, with respect to the reference point, of the cutting edge of the saw blade in the cut and a second sensor outputting a second signal representative of a force applied to the cutting edge of the saw blade. The saw also includes a chuck engageable with the saw blade. Accordingly, movement is constrained between the chuck and the saw blade. The saw also includes a motor that is operatively engaged with the chuck to oscillate the saw blade. The saw also includes a processor in electrical communication with the first and second sensors. The processor is configured in a first mode to output a third signal representative of the depth of penetration of the cutting edge of the saw blade when the cutting edge of the saw blade passes from the first medium to the second medium. The third signal may be based on the first and second signals.

A number of feature refinements and additional features are applicable to the seventh aspect. These feature refinements and additional features may be used individually or in any combination. As such, each of the following features that will be discussed may be, but are not required to be, used with any other feature or combination of features of the seventh aspect. For example, any of the forgoing features described with respect to any other aspect disclosed herein may be utilized with the seventh aspect.

For example, in an embodiment the first sensor may include a linear variable differential displacement transducer (LVDT), a digital encoder, an optical displacement sensor, or any other appropriate displacement sensor. In an embodiment, the second sensor includes a load cell. The third signal may be output when a second time derivative of the first signal is greater than zero and a first time derivative of the second signal is less than zero.

In an embodiment, the first sensor may be a linear variable differential displacement transducer (LVDT), the second sensor may be a load cell, and the third signal may be output when the second time derivative of the first signal is greater than zero and a first time derivative of the second signal is less than zero. That is, upon passing fully through the bone, the saw may undergo a decrease in force applied to the cutting edge and accelerate when the cut is complete. That is, monitoring the first and second sensor for this occurrence may allow the saw to be stopped upon completion of a cut. In an embodiment, the bone surrounded by a second medium with a density less than the bone such that upon completion of the cut the saw experiences the decrease in force against the cutting edge and acceleration of the blade.

In an embodiment, the system may include a mode selector and the processor may be configured to operate in a mode selected from the group of modes consisting of the first mode wherein the third signal corresponds to completely cutting through a structure and a second mode, wherein the processor is configured such that the third signal corresponds to when the saw blade has reached a predetermined depth for the cut. The first sensor may be a linear variable differential displacement transducer, the second sensor may be a load sensor, and the processor, in the first mode, outputs the third signal when a second time derivative of the first signal is greater than zero and a first time derivative of the second signal is less than zero, thus indicating the saw has passed through the bone. Also, the processor, in the second mode may output the third signal in response to the measured displacement equaling a predetermined depth.

In an embodiment, the third signal may include an alert perceivable by a user of the saw. The alert may be an auditory alert. Additionally or alternatively, the alert may include a change in speed of the motor of the saw. For example, the alert may include stopping the oscillation of the motor of the saw.

A eighth aspect includes a surgical instrument that includes an instrument working portion adapted to engage a portion of a patient to perform a surgical operation. The surgical instrument also includes a light emitter adapted to emit light in a direction toward the patient when the instrument working portion is engaged with the portion of the patient to perform the surgical operation.

A number of feature refinements and additional features are applicable to the eighth aspect. These feature refinements and additional features may be used individually or in any combination. As such, each of the following features that will be discussed may be, but are not required to be, used with any other feature or combination of features of the eighth aspect. For example, any of the forgoing features described with respect to any or all of the foregoing aspects may be utilized with the eighth aspect.

For example, in an embodiment, the surgical instrument may correspond to any of the foregoing saw embodiments for determining a depth of penetration of a saw blade in a cut. However, in other embodiments, the surgical instrument may comprise other types of surgical saws, a surgical grinder, a surgical chisel, or some other surgical instrument without limitation.

In an embodiment, the light emitter may include a light emitting diode (LED) light source. For instance, in an embodiment, the light source may be disposed within a housing of the surgical instrument. Alternatively, the light source may be disposed remotely from the surgical instrument and transmitted to the light emitter (e.g., by way of fiber optics or the like).

In an embodiment, the surgical instrument may include a measurement system for determining, with respect to a reference point, a depth of the instrument working portion when the instrument working portion passes from a first medium to a second medium. As such, any of the foregoing discussion with respect to embodiments of measurement systems may be provided in various embodiments without limitation. For instance, the surgical instrument may include a first sensor outputting a first signal representative of a displacement, with respect to the reference point, of the instrument working portion, a second sensor outputting a second signal representative of a force applied to the instrument working portion, and a processor in electrical communication with the first and second sensors. The processor may be configured in a first mode to output a third signal representative of the depth of penetration of the instrument working portion of the surgical instrument when the instrument working portion passes from the first medium to the second medium, the third signal based on the first and second signals.

In an embodiment, the light emitter may be selectively operable between two emitting states (i.e., always on and trigger depression) and a non-emitting state. For instance, the emitting state may occur upon operation of the instrument working portion, and the non-emitting state may occur upon cessation of operation of the instrument working portion. Additionally or alternatively, the light emitter may be selectively changed between the emitting state and non-emitting state by way of a state switch or the like.

A ninth aspect includes a saw including a saw blade penetration measurement system for determining, with respect to two reference points, completion of a cutting operation when the cutting edge of the saw blade passes from a first medium to a second medium, the first medium contiguous with the second medium, the first medium having a first density, the second medium having a second density. The saw may include first and second sensors for outputting, independently, the displacement of the saw blade relative to reference points established by each of the first and second sensors. A third sensor outputting a third signal representative of a force applied to the cutting edge of the saw blade may also be provided. The saw also includes a chuck engageable with the saw blade. Accordingly, movement is constrained between the chuck and the saw blade. The saw also includes a motor that is operatively engaged with the chuck to oscillate the saw blade. The saw also includes a processor in electrical communication with the first, second and third sensors. The processor is configured in a first mode to output a fourth signal representative of when the cutting edge of the saw blade passes from the first medium to the second medium based on at least one of the first, second or third signals (i.e., when the saw passes completely through a medium to be cut).

A number of feature refinements and additional features are applicable to the ninth aspect. These feature refinements and additional features may be used individually or in any combination. As such, each of the following features that will be discussed may be, but are not required to be, used with any other feature or combination of features of the ninth aspect. For example, any of the forgoing features described with respect to any other aspect disclosed herein may be utilized with the ninth aspect.

Additionally, in an embodiment the first and sensors include a linear variable differential displacement transducer (LVDT). In an embodiment, the third sensor includes a load cell. The fourth signal may be output when a second time derivative of the first or second signal is greater than zero and a first time derivative of the third signal is less than zero.

In an embodiment, the first and sensors may be a linear variable differential displacement transducer (LVDT), the third sensor may be a load cell, and the fourth signal may be output based on the first, second, and/or third sensor outputs (e.g., when the second time derivative of one of the first and second signals is greater than zero and a first time derivative of the third signal is less than zero). In some embodiments, absolute values of force and displacement may also be used. In an embodiment, the first medium may be a bone surrounded by the second medium (e.g., air or surrounding soft tissue).

The system may include a mode selector and the processor may be configured to operate in a mode selected from the group of modes consisting of the first mode wherein the fourth signal corresponds to a condition when the saw has passed completely through the bone. In a second mode, the processor is configured such that the fourth signal corresponds to a when the saw blade has reached a predetermined depth of the cut. In this regard, the first and second sensors may be linear variable differential displacement transducers, the third sensor may be a load sensor, and the processor, in the first mode, outputs the fourth signal when a second time derivative of one of the first and second signals is greater than zero and a first time derivative of the third signal is less than zero. Also, the processor, in the second mode, may output the fourth signal in response to one or both of the first and second sensors outputting a signal corresponding to the predetermined depth.

In an embodiment, an output device presents an alert perceivable by a user of the saw based on the fourth signal. The alert may be an auditory alert. Additionally or alternatively, the speed of the motor of the saw is changed based on the fourth signal. For example, the oscillation of the motor of the saw is stopped based on the fourth signal.

A tenth aspect includes a sawing assembly having a displacement sensor for performing an automatic disabling of cutting when a predetermined cutting depth has been determined. The assembly includes a cutting guide or cutting jig, a saw having a blade and a displacement sensor for outputting a signal representative of a displacement of the saw blade with respect to a reference point. The saw blade has a cutting edge disposed at a distal end of the saw blade. The saw blade includes a shank that is adapted for engagement with a drive assembly that provides an oscillating motion of the saw blade. The cutting guide or cutting jig includes one or more apertures sized to receive at least a portion of the saw blade or shank through the aperture. As such, the cutting guide or cutting jig guides the saw blade in a direction along a cutting direction of the saw blade.

A number of feature refinements and additional features are applicable to the tenth aspect. These feature refinements and additional features may be used individually or in any combination. As such, each of the foregoing features described above may be, but are not required to be, used with any other feature or combination of features of the tenth aspect.

BRIEF DESCRIPTION OF THE FIGURES

FIG. 15A is a perspective view of an embodiment of a saw including two saw blade penetration measurement devices;

FIGS. 21A-21C depict a progression for engagement of a saw blade assembly with the saw FIG. 19.

DETAILED DESCRIPTION

Figure 1:
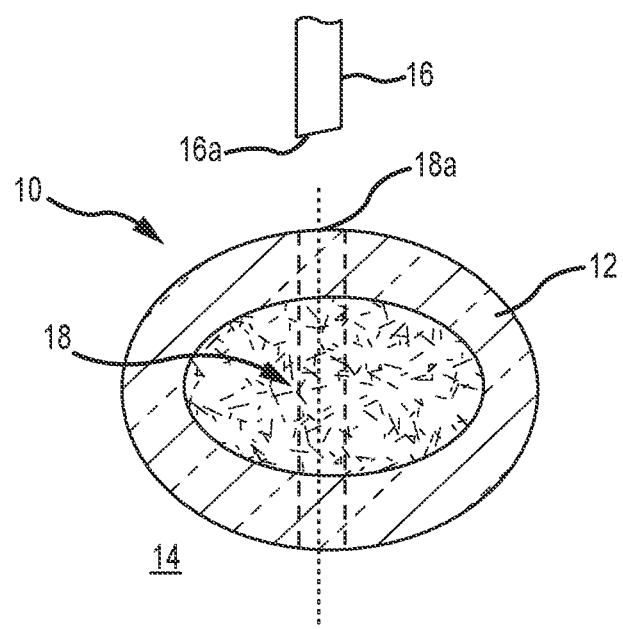
FIG. 1 is a sectional view of a bone illustrating a prior art method of using a saw mechanism to create a bicortical path through a cortical bone having multiple layers.
Figure 2:
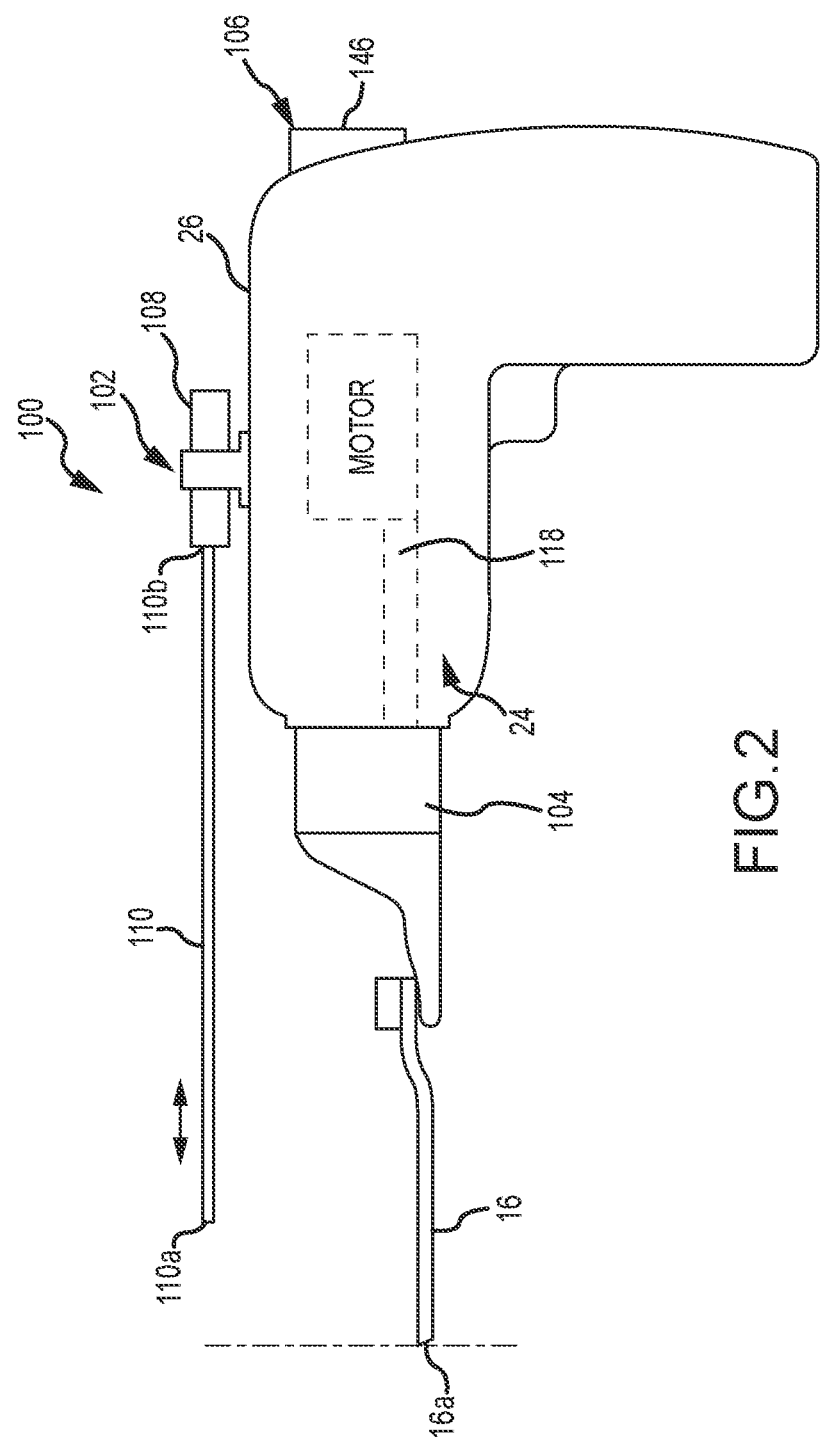
FIG. 2 is an elevation view of an embodiment of a real-time, saw blade penetration measurement system.
Figure 3:
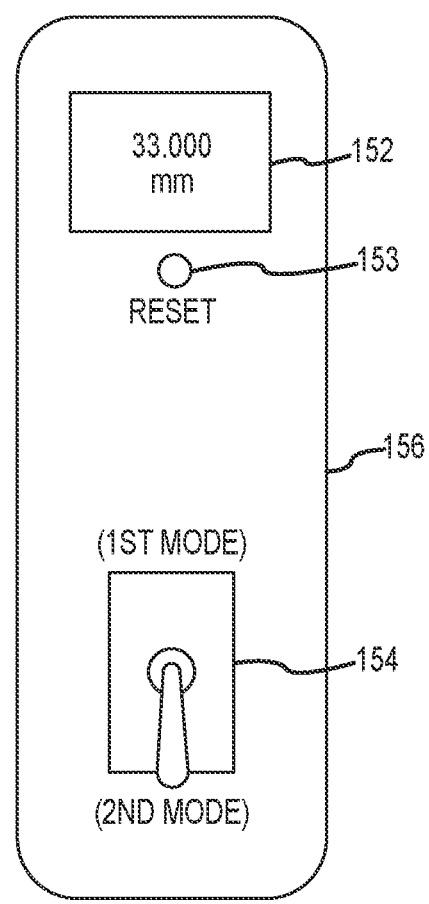
FIG. 3 is an elevation view of an embodiment of a control panel of a controller assembly of FIG. 2.
Figure 4:
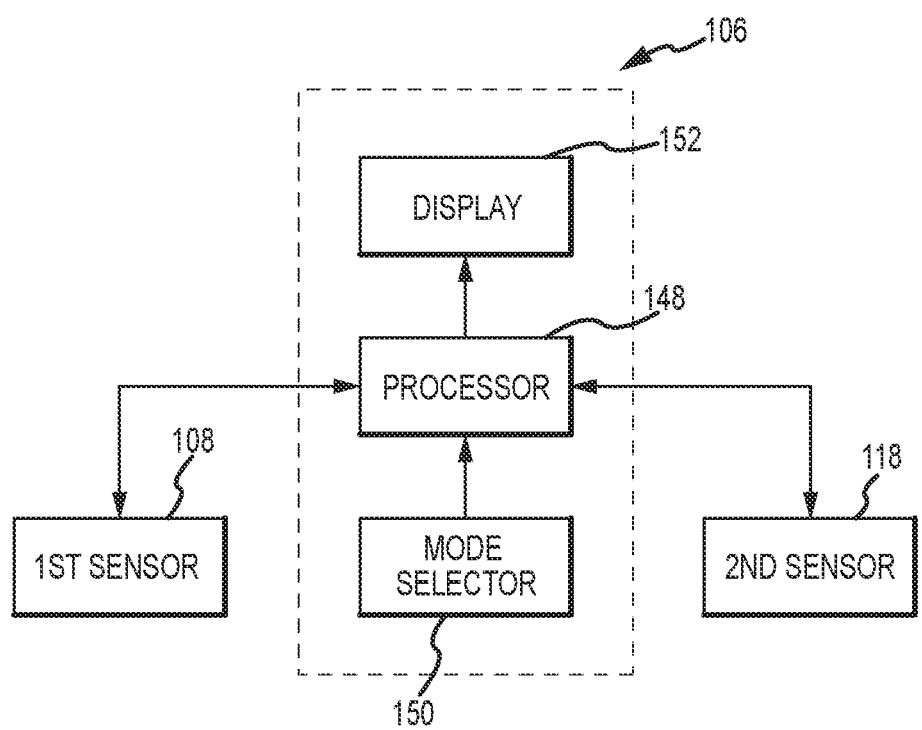
FIG. 4 is a schematic block diagram of the controller assembly of FIG. 2 and the inputs and outputs of the controller assembly.
Figure 5:
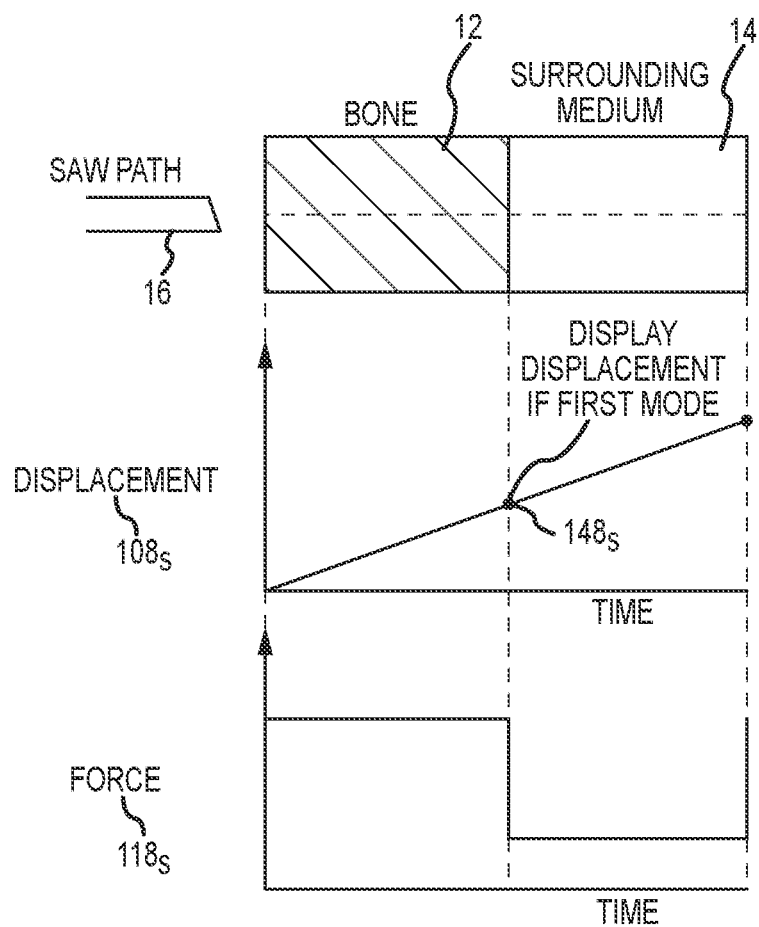
FIG. 5 is a diagram illustrating the position of the saw blade of FIG. 2 and the corresponding output of the first and second sensors of the displacement and load measurement assemblies of FIG. 2.

Certain terminology is used in the following description for convenience only and is not limiting. The words "right," "left", "lower" and "upper" designate directions in the drawings to which reference is made. The words "inwardly" and "outwardly" refer to directions toward and away from, respectively, the geometric center of the saw blade penetration measurement system and designated parts thereof. The terminology includes the words above specifically mentioned, derivatives thereof and words of similar import.

Additionally, as used in the claims and in the corresponding portion of the specification, the word "a" means "at least one". Further, unless otherwise defined the word "about" when used in conjunction with a numerical value means a range of values corresponding to the numerical value plus or minus ten percent of the numerical value. Still further, the word "or" has the meaning of a Boolean inclusive "Or". For example, the phrase "A or B" means "A" alone or "B" alone or both "A" and "B".

Figure 8:
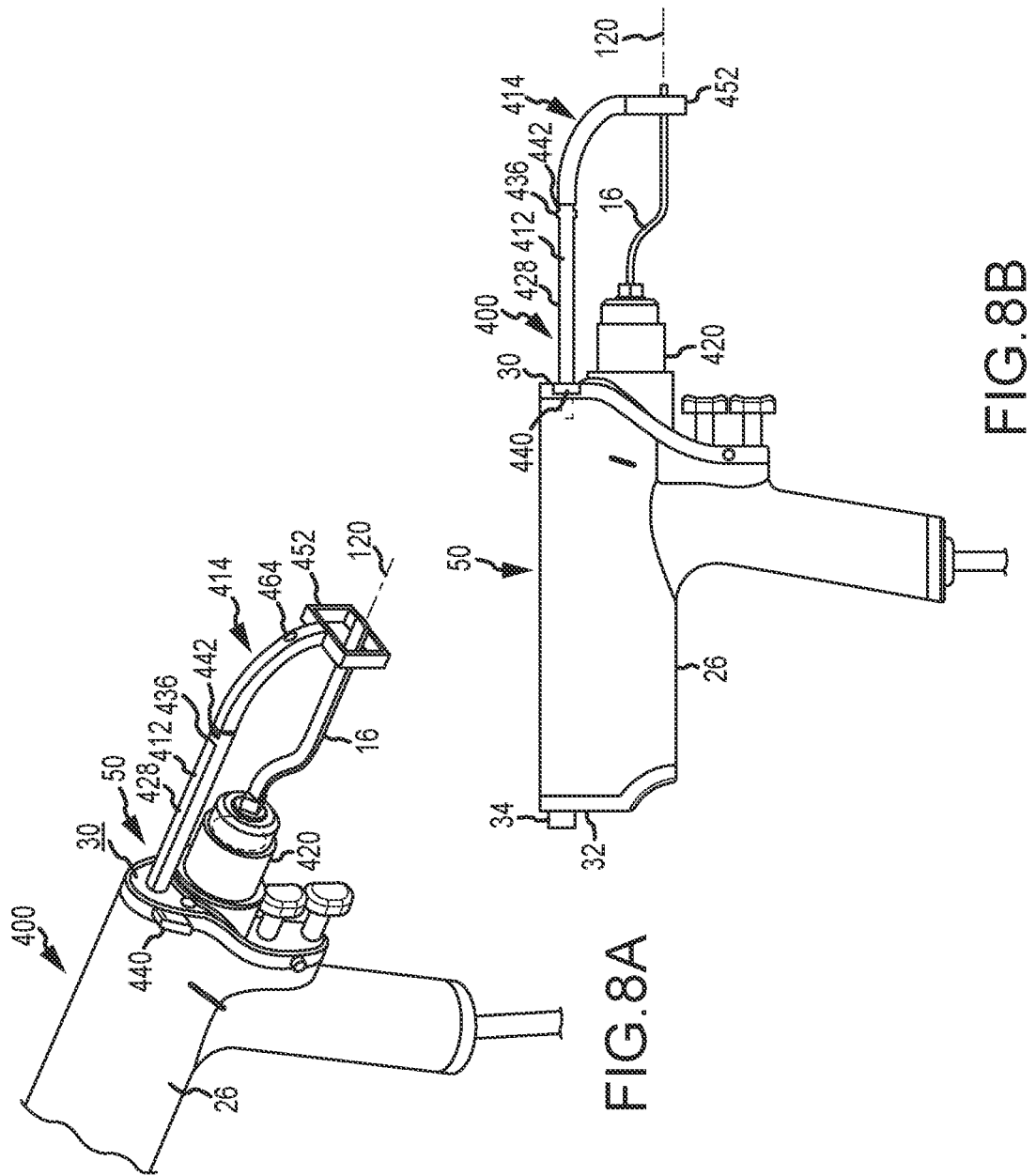
FIGS. 8A and 8B are perspective and side views, respectively, of an embodiment of a saw including a saw blade penetration measurement system.

Referring to the drawings in detail, where like numerals indicate like elements throughout there is shown a first embodiment of the saw blade penetration measurement system generally designated 100, and hereinafter referred to as the "measurement system" 100, in accordance with the present invention. The measurement system 100 is for determining, with respect to a reference point (not shown), a depth of penetration of the cutting edge 16a of a saw blade 16 in a cut. The saw blade 16 may be oscillated by a drive 24 in a saw housing 26 of any typical well known surgical saw. In this regard and as may be appreciated below, a measurement system 100 may be provided with an existing surgical saw (e.g., as a retrofit). In further embodiments described in greater detail below, a measurement system 400 may be provided that is at least partially integrated into a saw 50 (e.g., as shown in FIGS. 8A-8C) and/or saw 700 shown in FIGS. 18-21C.

Referring to FIGS. 2, 5A, 5B and 5C, the measurement system 100 may include a saw blade displacement measurement assembly 102, a saw blade load measurement assembly 104, and a controller assembly 106. The displacement measurement assembly 102 is connected to the saw housing 26. The connection can be made by a variety of well known mounting methods such as a mount that clamps to the displacement measurement assembly 102 and is attached to the saw housing 26 by one or more threaded fasteners. Alternative methods such as welding or adhesive bonding could also be used. The displacement measurement assembly 102 may include a first sensor 108 that outputs a first signal 108s representative of a displacement, with respect to the reference point, of the cutting edge 16a of the saw blade 16 in the cut being sawed. The displacement measurement assembly 102 preferably has an extension 110 that is displaceable along a direction of sawing. The extension 110 has a distal end 110a that can be placed in registry with the reference point when the cutting edge 16a of the saw blade 16 is positioned at the outer surface of the medium to be cut and maintained in registry with the reference point throughout the sawing process. The reference point may be any anatomical structure proximal to the desired location of the cut to be sawed. Additionally or alternatively, the reference point may be established using a bushing disposed relative to the saw blade or with respect to a cutting guide as will be described in greater detail below. The extension 110 has a proximal end 110b that is attached to the first sensor 102. In one embodiment, the sensor 102 may be a linear variable differential displacement transducer ("LVDT"), although other appropriate displacement sensors may also be used as described in greater detail below.

A second sensor 118 may be located within the housing 26 outputs a second signal representative of a force applied to the cutting edge 16a of the saw blade 16. In one embodiment, the second sensor 118 may be a hydraulic pressure transducer and a portion within the housing 26 and/or the drive 24 may form a hydraulic chamber connecting the second sensor 118. In another embodiment, the second sensor 118 may include a load cell, such as a piezo-electric device, located within the housing 26 and/or the drive 24. An electrical conductor electrically connects the piezo-electric device to the controller assembly 106. In this regard, it may be appreciated that depending upon the drill configuration, the second sensor 118 may be arranged in various manners relative to the saw blade 16. For instance, in a sagittal saw or an ultrasonic saw, an axial force (i.e., extending between the cutting edge and the attachment of the saw blade to the saw) may be applied relative to the distal cutting edge of the saw blade such that the second sensor 118 may measure the axial force to determine the force acting on the cutting edge. In a reciprocating saw, the load may be transverse (i.e., orthogonal to the attachment of the saw blade to the saw). Thus, the second sensor 118 may be configured to measure the load acting on the cutting edge, which may be orthogonal to an axis defined along the attachment of the saw blade to the saw.

The controller assembly 106 is in electrical communication with the first sensor 108 and/or the second sensor 118. In an embodiment, the controller assembly 106 has a controller housing 146 integral with the saw housing 26. However, with further reference to FIG. 13A, the controller housing 146 may also be provided as a remote unit. The controller assembly 106 includes a processor 148 in electrical communication with the first and second sensors 108, 118 and with a mode selector 150 having a mode selector switch 154 and a display 152 having a reset button 153. The display 152, the reset button 154 and the mode selector switch 154 may be mounted in a panel 156 of the controller housing 146. Alternatively, the display 152 or the reset button 153 or the mode selector 154 or any combination thereof could be separately housed in the remote control unit that communicates with the first and second sensors 108, 118 by a wired or wireless link. Furthermore, the reset button 153 may be provided as a separate hardware portion such as a foot pedal or the like. In this regard, the hardware portion comprising the reset button 153 be in wired or wireless communication with the controller assembly 106. In this regard, the foot pedal may be used to set or reset the reference point of the controller and/or to indicate a new sawing operation. The display 152 is for indicating the measured displacement of the cutting edge 16a of the saw blade 16 to the user. The display 152 is controlled by the processor 148. The display 152 may continuously indicate the changing displacement of the cutting edge 16a of the saw blade 16 during the sawing of a cut and may also indicate the depth of the cut at the when the saw blade 16 passes from one medium to another (i.e., when the saw has passed completely through a bone).

Figure 13A:
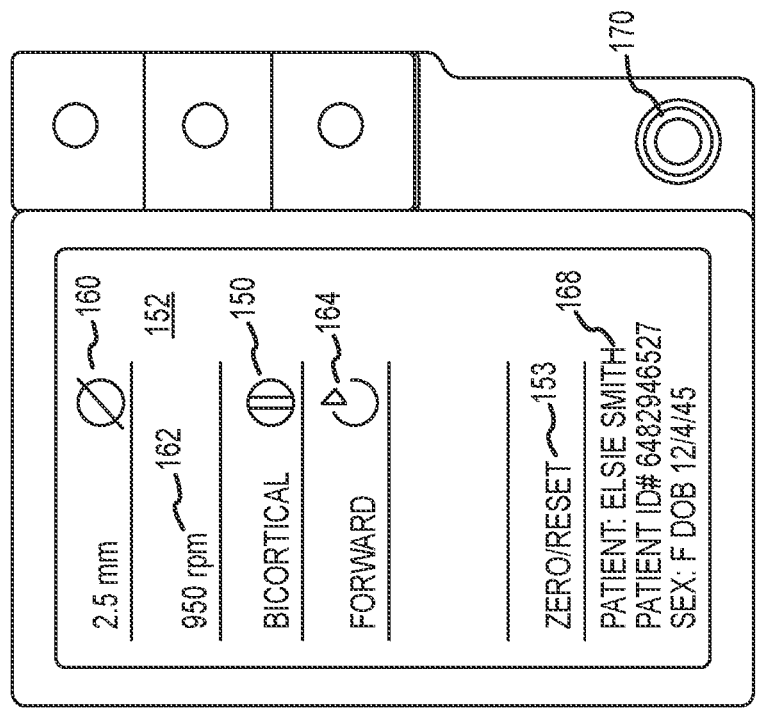
FIGS. 13A and 13B depict an embodiment of a controller for use in operation of a saw having a saw blade penetration measurement system.
Figure 13B:
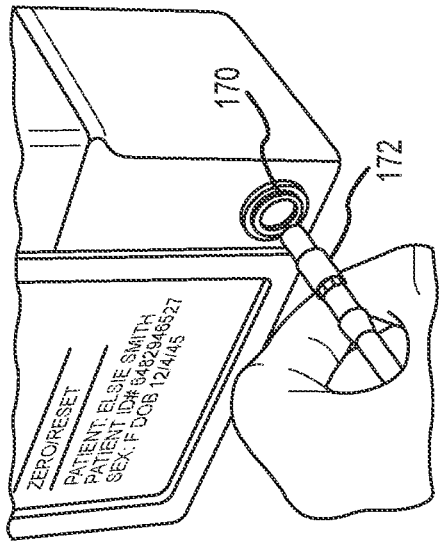

For instance, with continued reference to FIGS. 13A and 13B, the display 152 may be a touch sensitive display (e.g., a resistive or capacitive type touch screen display). The display 152 may include an indication of a cut length 160, the saw speed 162, etc. The display 152 may also include patient information 168. The controller unit 106 may include a port 170 for engagement of a wired plug connection 172 with the saw 50. In this regard, the saw 50 may be connected to the controller assembly 106 to supply power to the saw 50 and communicate data between the saw 50 and the controller assembly 106

Referring to FIGS. 1, 3, 4, 5, the processor 148 may be configured to operate in a first mode for cut length measurement for a cut that extends through the entirety of the medium to be cut. Thus, with reference to FIG. 5, the processor 148 may be configured to output a third signal 148s representative of the depth of penetration of the cutting edge 16a of the saw blade 16 when the cutting edge 16a of the saw blade 16 passes from a first medium having a first density (i.e., bone 12) to the second medium having a second density (i.e., a surrounding medium 14 such as air or soft tissue). The third signal 148s may be based on the first and second signals 108s, 118s. Preferably, the third signal 148s is output at a second time derivative of the first signal 108s being greater than zero and a first time derivative of the second signal 118s being less than zero. In other words a positive acceleration of the saw blade 16 and a concurrent reduction in the force applies to the cutting edge 16a of the saw blade 16 trigger the third signal 148s. However, the third signal 148s may also be based on other mathematical transforms of the first or second signals 108s, 118s or raw values of the first signal 108s or 118s. For instance, the third signal 148s may be based on the first and/or second derivative of the first signal 108s (e.g., the displacement signal). For instance, the third signal 148s may be generated upon a concurrent positive state of the first signal 108s, a first derivative of the first signal 108s with respect to time (e.g., a velocity signal), and a second derivative of the first signal 108s with respect to time (e.g., an acceleration signal). In this regard, any one or more of the displacement signal, the velocity signal, and acceleration signal may be actually measured to derive the displacement signal, a velocity signal, and acceleration signal. Thus, the third signal 148s may be dirt derived using a single sensor, such that the force sensor described above in an embodiment of the saw may not be employed in all embodiments.

The processor 148 is also configured to operate in a second mode for saw blade penetration measurement (e.g., using the mode selector 150 and mode selector switch 154). The second mode of operation is directed to the case where a predetermined depth is established. As such, the processor 148 may monitor the first signal 108s to determine when the predetermined depth is reached. Once reached, the third signal 148s may be output. In this regard, the value of the first signal 108s alone may be used in the second mode of operation to cease the sawing when the predetermined depth is reached. As may be appreciated, rather than the second time derivative of the first signal 108s that indicates an acceleration of the blade, the value of the signal 108s alone may be utilized. That is, a "saw-to-depth" mode may be established where the saw operate until a predetermined depth to reach is determined by the first signal 108s, and thereupon the operation of the saw is terminated once the predetermined depth is reached.

Additionally or alternatively, the third signal 148s may be at least partially based on additional parameters other than the first signal 108s and second signal 118s. For instance, in at least some embodiments, the third signal 148s may be at least partially based on a parameter associated with the oscillation of the saw blade 16. For instance, the speed of the drive 24 oscillating the saw blade 16, the resistance against the saw blade (e.g., is measured by the load on a motor driving oscillation of the saw blade), or another appropriate parameter regarding the oscillation of the blade 16 may be utilized in outputting the third signal 148s. Further still, parameters such as the length of the cutting edge of the saw blade 16, the bone to be sawed, or other appropriate parameters may be utilized in determining the third signal 148s.

Furthermore, the generation of the third signal 148s may at least partially be customized based on the patient. In this regard, information regarding the patient may be provided to the controller assembly 106 and utilized by the processor 148 in determining the third signal 148s. For instance, a patient's age, sex, and/or other demographic information may be provided. As may be appreciated, the demographic data of the patient may provide a correlation to expected bone density or other parameter regarding an expected property of the patient's anatomy based on the demographic data of the patient. In this regard, the demographic data may be used to correlate an expected parameter associated with the patient's anatomy (e.g., bone density) that may be used as a factor in generation of the third signal 148s. In addition, direct measurement of an anatomical parameter (e.g., bone density) for a given patient may be provided directly to the controller assembly 106, thereby potentially eliminating the need to estimate the parameter based on demographic data.

Figure 6:
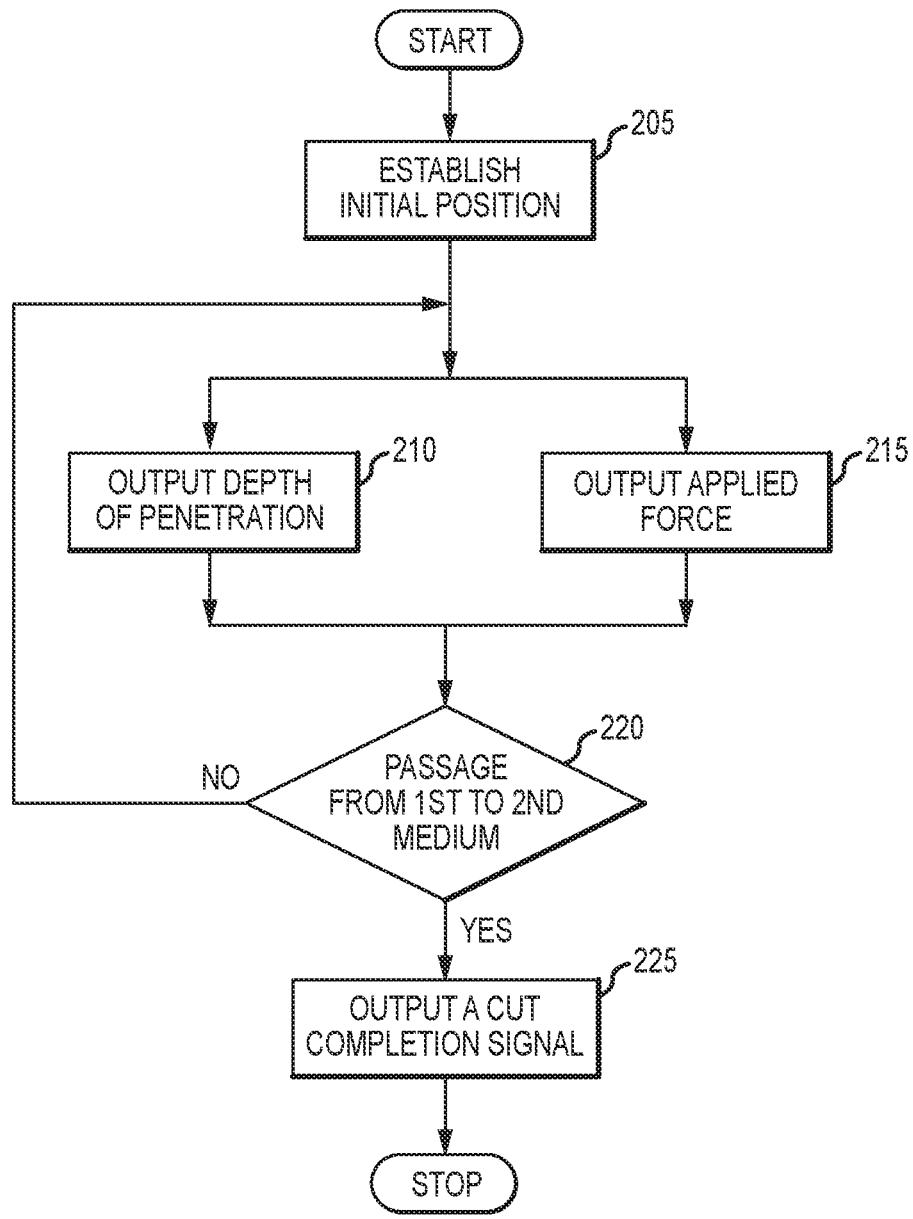
FIG. 6 is a flow diagram of an embodiment of a method for determining the depth of penetration of a saw blade.

Referring to FIG. 6, there is shown a block diagram of a first method for determining, with respect to a reference point, the depth of penetration of the cutting edge 16a of a oscillating saw blade 16 in a cut when the cutting edge 16a of the saw blade 16 transitions from a first medium having a first density, such as the hard outer cortex 12 of a cortical bone 10, to a second adjacent medium 14 having a second density, such air or tissue surrounding the outer surface of the cortical bone 10. (FIG. 1B).

An initial position of the cutting edge 16a of the saw blade 16 relative to the reference point is established (Step 205). The initial position may be established by placing the cutting edge 16a of the saw blade 16 against the outer surface of the cortical bone to be sawed and by extending the distal end 10a of the extension 110 of the displacement measurement assembly 102 to the reference point, such as an anatomical structure proximal to the desired location of the cut to be created. As will be appreciated in the discussion of the embodiments below, the reference point may also be established by a bushing member of a saw blade assembly that is engaged with a displacement sensing arm of a displacement sensor. For instance, the bushing member may have a reference surface contactable with the bone to be sawed. Further still, the reference point may be established relative to a cutting guide or the like.

In any regard, with the cutting edge 16a of the saw blade 16 and the measurement system reference point in the above positions (i.e., aligned at a surface of the medium to be sawed), the measured displacement of the saw blade 16 is set to zero by pressing the reset button 153. Upon commencement of sawing, a first signal representing the depth of penetration of the cutting edge 16a of the saw blade 16 in the cut is output (Step 210). A second signal representing a force applied to the cutting edge of the saw blade is output (Step 215). A third signal based on the first and second signals and representative of when the cutting edge of the saw blade passes from the first medium to the second medium is output (Step 225). Preferably, the third signal is output when the second time derivative of the first signal is greater than zero and a first time derivative of the second signal is less than zero. Additionally or alternatively and as described above, the third signal may be based only on the first signals and/or mathematical transforms thereof.

The third signal may cause an output device to generate an alert that may be perceivable by a user of the saw. As such, upon determination that the saw has passed through the bone (e.g., as described above), the alert may provide feedback to the user that the bone has been sawed through. As such, the alert may be an auditory alert such as a tone or the like. In another embodiment, the third signal may cause a change in the speed of the motor of the saw. For instance, the saw may be slowed such that the user may be alerted to the fact that the saw has passed through the bone. Further still, the saw may be automatically stopped at the occurrence of the third signal. It may be appreciated that any other user perceivable alert may be provided including, for example, a visual, tactic, or other type of user perceivable feedback.

Figure 7:
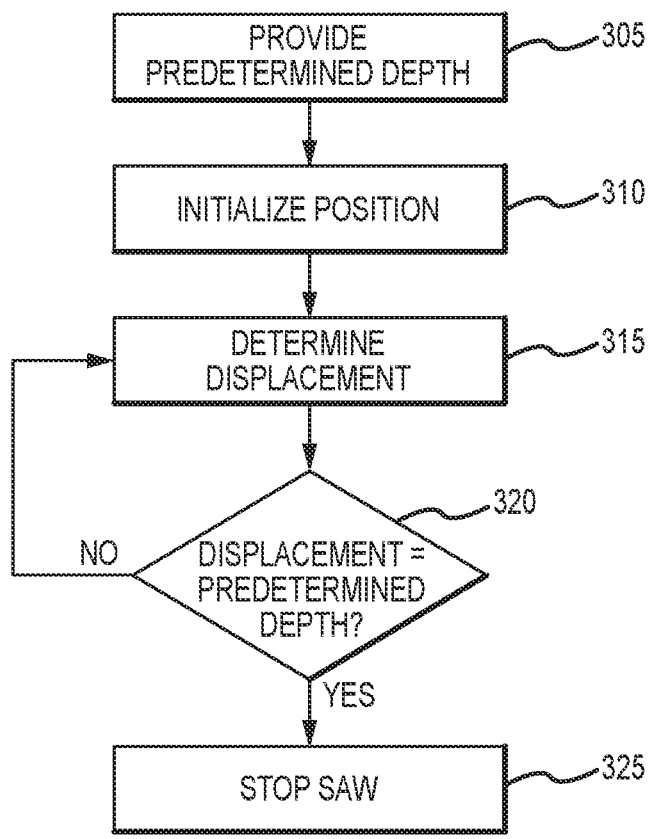
FIG. 7 is a flow diagram of an embodiment method for determining the depth of penetration of a saw blade.

Referring to FIG. 7, there is shown a block diagram of a second method for determining, with respect to a reference point, the length of a cut. The predetermined depth to be reached by the saw blade is provided (Step 305). An initial position of the cutting edge 16a of the saw blade 16 relative to the reference point is established (Step 310), preferably in a manner similar to Step 205 discussed above. The displacement of the cutting edge 16a of the saw blade 16 is continuously determined (Step 315). The processor 148 may determine if the displacement of the cutting edge 16a of the saw blade is equal to the predetermined depth provided in Step 305. If the depth does not equal the predetermined depth (i.e., is less than the predetermined depth), the cutting procedure may continue. Once the displacement equals the predetermined depth, the saw may be stopped (Step 325).

The components used to construct the present invention may include a variety of materials that are customarily used in the manufacture of surgical saws. One having ordinary skill in the art will readily appreciates the materials that most desirably may be used to construct the present invention. In one embodiment, however, the sawing mechanism, saw blade displacement measurement assembly, the saw blade load measurement assembly and the structural elements of the controller assembly may be constructed of a combination of polymeric materials (e.g., high strength plastic), polymers and stainless steel.

One embodiment of a saw with an improved displacement sensor including a displacement sensing arm that extends from the saw may be provided. For example, such a displacement sensing arm may be provided that may coordinate with a bushing member of a saw blade assembly that may be used with the saw. However, other embodiments are described below where the displacement sensing arm may coordinate (e.g., contact or be engaged with) a cutting guide to establish a reference point. However, in the case of a bushing, the bushing may move along the saw blade in a direction corresponding to the direction of cutting. Upon engagement of the bushing and the displacement sensing arm, the bushing and displacement sensing arm may undergo corresponding movement. As such, the bushing may be disposed in contact with the medium to be sawed when the cutting edge of the saw blade is in contact with the medium. As such, a reference point may be established when the bushing and cutting edge of the saw blade are both in contact with the medium to be sawed. As the bushing is located adjacent to (e.g., partially or fully surrounding the saw blade or operatively engaged with the saw blade), the bushing may facilitate contact with the medium at or very near the location to be sawed prior to creating a cut as described above. In this regard, the reference point may be more accurately maintained as the bushing may contact at least a portion of a periphery of the cut created in the medium sawed. That is, the bushing may remain in intimate contact with the medium to be sawed adjacent to the cut created. This may prevent false displacement readings attributable to the foregoing problems associated with an offset extension 110. Furthermore, the amount of contact of the saw may be localized at the location to be sawed, thus allowing for potentially less intrusion when performing sawing operations.

For example, with additional reference to FIGS. 8A-8C and 9, an embodiment of a saw 50 with a measurement system 400 is shown. The saw 50 may integrally include at least some components of the measurement system 400 to facilitate operation of the measurement system 400 in connection with the saw 50 (e.g., which may be according to the description above regarding measurement system 100). For example, at least a portion of a displacement sensor 410 may be integrated into a housing 26 of the saw 50. In this regard, the displacement sensor 410 may include a depth sensing arm 412 that is specifically adapted for engagement with a bushing 452 of a saw blade assembly 60 that may be engaged by the chuck 420 of the saw 50.

In this regard, the depth sensing arm 412 may be used to establish a reference point from which displacement of the saw blade 16 may be measured as described above. In this regard, as follows herein, a general description of the features and operation of the saw 50 used in conjunction with the saw blade assembly 60 is provided.

Figure 9:
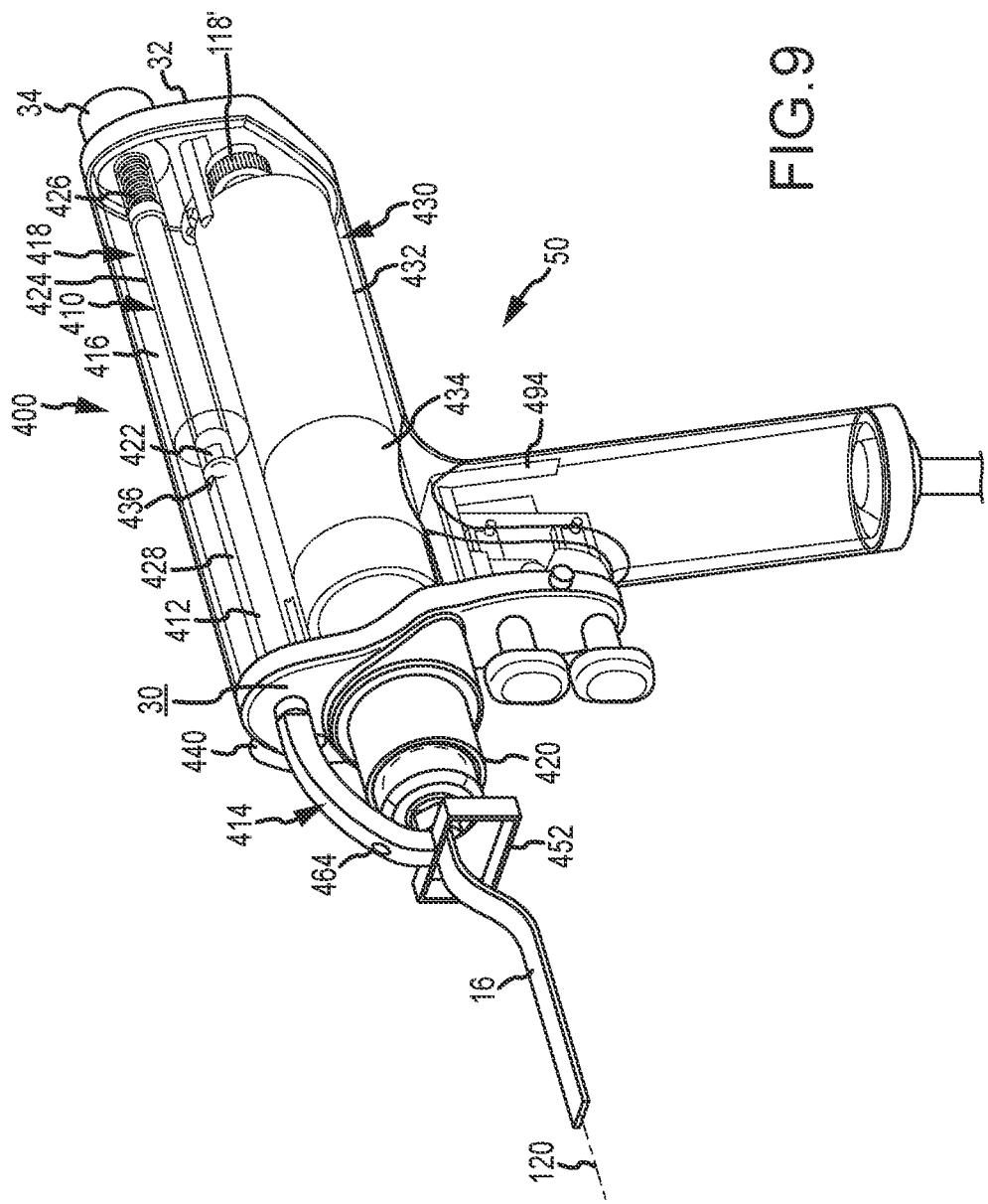
FIG. 9 is a perspective view with a partial cutaway of a saw body of an embodiment of a saw including a saw blade penetration measurement system.

As may be appreciated in FIGS. 8A-8C, the displacement sensor 410 may include a depth sensing arm 412 that may extend from the saw housing 26. For example, the depth sensing arm 412 may extend distally (e.g., from a distal face 30 of the saw housing 26) in a direction corresponding with the direction in which the saw blade 16 extends from a chuck 420 of the saw 50. At least a portion of the displacement sensing arm 412 may extend from the saw housing 26 parallel to a cutting direction 120 of the saw 50. The depth sensing arm 412 may also include a distal portion 414 that is adapted to engage a bushing 452 provided with the saw blade assembly 60. As used herein, distal may correspond to a direction from the saw 50 toward the cutting edge 16a of the saw blade 16 and proximal may correspond to a direction from the cutting edge 16a of the saw blade 16 toward the saw 50. In this regard, at least a portion of the depth sensing arm 412 (e.g., the distal portion 414) may be adapted to engage the bushing 452 of the saw blade assembly 60 as will be described in more detail below. In any regard, at least a portion of the depth sensing arm 412 may extend into the housing 26. With further reference to FIG. 9, the housing 26 may contain a coil 416. As such, a proximal end 418 of the displacement sensing arm 412 may interface with the coil 416 of the displacement sensor 410 that may be disposed within the saw housing 26.

Specifically, in FIG. 9, the depth sensing arm 412 is shown in a retracted position relative to the saw blade 16. As such, this retracted position shown in FIG. 9 may occur when the saw blade 16 is advanced relative to the bushing 452 during sawing (e.g., such that the portion of the saw blade extending beyond the distal edge of the bushing 452 would be disposed in the medium to be sawed). In this regard, the proximal end 418 of the displacement sensing arm 412 is disposed within the coil 416 of the displacement sensor 410. Accordingly, the displacement sensor 410 may comprise an LVDT sensor as described above that is adapted to sense the position of a core 422 relative to a coil 416. The displacement sensing arm 412 may incorporate a core 422 at the proximal end 418 thereof. Accordingly, as the proximal end 418 of the displacement sensing arm 412 is moved relative to the coil 416, the location of the core 422 may be determined to provide an output corresponding to the position of the core 422, and in turn the displacement sensing arm 412 relative to the saw housing 26. That is, the depth sensing arm 412 may be displaceable relative to the coil 416 such that the displacement sensor 410 may be operable to sense a change in position of the depth sensing arm 412 relative to the saw housing 26 and output a measure of the displacement that may be used as described above in determining a depth of a cut. In an embodiment, the total measurable travel of the core 422 relative to the coil 416 may be at least about 2.5 in (6.4 cm). Furthermore, the resolution of the output of the displacement sensor 410 may be about 0.1% (e.g., about 0.002 inches (0.06 mm) for a sensor having a total measureable travel of 2.5 inches).

While a LVDT displacement sensor is shown and described in relation to the saw 50 shown in the accompanying figures, it may be appreciated that other types of displacement sensors may be provided. For instance, the sensor may provide for the absolute or relative measurement of the position of the distal end 418 of the displacement sensing arm 412 to provide a displacement measure. For instance, in another embodiment, an optical displacement sensor may be provided. Other types of displacement sensors are also contemplated such as, for example, a capacitive displacement sensor, ultrasonic sensors, Hall effect sensors, or any other sensors known in the art capable of outputting an absolute or relative position measure.

In an embodiment, the coil 416 may define a passage 424 extending at least partially through the housing 26. Specifically, the passage 424 may extend from a proximal face 32 of the housing 26 to the distal face 30 of the housing 26. That is, the passage 424 may extend entirely though the housing 26. An end cap 34 may be provided that is operable to close the proximal end of the passage 424 at the proximal face 32 of the saw housing 26. Furthermore, a biasing member 426 (e.g., a coil spring) may be provided in the passageway 424 at a proximal end thereof. The biasing member 426 may be provided between the end cap 34 and the proximal end 418 of the displacement sensing arm 412. In this regard, the biasing member 426 may act on the proximal end 418 of the displacement sensing arm 412 to bias the displacement sensing arm 412 distally relative to the passage 424 and saw housing 26.

As such, the displacement sensing arm 412 may include features that selectively prevent ejection of the displacement sensing arm 412 from the distal end of the passage 424. For example, the displacement sensing arm 412 may include at least one flat 428 that extends along a portion of the arm 412. At the proximal and distal extents of the flat 428, the displacement sensing arm 412 may include shoulders 436 that project from the flats 428 (best seen at the distal portion 414 in FIG. 8B and at the proximal portion 418 in FIG. 9). As such, at the proximal opening of the passage 424, a selectively displaceable stop 438 may be disposed relative to the flat 428 such that the flat 428 may move relative to the stop 438, but interfere with the shoulder 436 defined in the displacement sensing arm 412 to prevent passage of the shoulder 436 beyond the stop 438. In this regard, the length of the displacement sensing arm 412 along which the flat 428 extends may be moveable relative to the stop 438, and the stop 438 may limit proximal and distal movement of the displacement sensing arm 412 beyond the stop 438.

However, the stop 438 may be displaceable upon depressing, for example, a button 440 provided on an exterior of the housing 26. Thus, upon depressing the button 440, the stop 438 may be displaced away from the displacement sensing arm 412 to allow the shoulder 436 to pass distally from the distal end of the passage 424 such that the displacement sensing arm 412 may be removed entirely from the passage 424. The distal end of the flats 438 may include a detent 442 that may be engageable with the stop 438 so as to maintain the displacement sensing arm 412 in a proximally disposed, retracted position relative to the housing (e.g., as shown in FIG. 9). Once the button 440 is depressed and released, the detent 442 at the proximal end of the flat 428 of the displacement sensing arm 412 may be released by the stop 438 and the displacement sensing arm 412 may move proximally (e.g., under influence of the biasing member 426). The displacement sensing arm 412 may move proximally until the shoulder 436 at the distal end of the flat 428 are engaged to prevent further distal movement of the displacement sensing arm 412. Accordingly, the displacement sensing arm 412 may be retained in a retracted position (e.g., for improved visibility of the distal end of the saw blade 16), released to be moveable relative to and biased proximally with respect to the housing 26, and removable altogether from the housing 26.

In the latter regard, removal of the displacement sensing arm 412 and biasing member 426 from the passage 424 may allow for separate cleaning (e.g., in an autoclave) of those members. Additionally, removal of the end cap 34 may allow for a cleaning apparatus (e.g., a brush or the like) to be passed through the full length of the passage 424 to facilitate cleaning thereof.

As referenced above, the distal portion 414 of the displacement sensing arm 412 may be adapted to engage a saw blade assembly 60 (e.g., a bushing 452 thereof) that is correspondingly adapted for use with the saw 50. For instance, as shown in FIGS. 8A-8B and FIG. 9, the displacement sensing arm 412 may generally be linear along the proximal portion 418 of the displacement sensing arm 412. In this regard, the proximal portion 418 may be adapted to be collinear with the passage 424 and moveable within the passage 424.

Furthermore, the distal portion 414 of the displacement sensing arm 412 (e.g., the portion distal to the linear portion of the displacement sensing arm 412) may extend from the linear portion of the displacement sensing arm 412 toward the saw blade assembly 60 that may be engaged by the chuck 420 of the saw 50. In this regard, the linear portion of the displacement sensing arm 412 may be substantially parallel to and offset from the cutting direction 120. The distal portion 414 may extend from the linear portion in a direction corresponding with the offset such that the distal portion 414 extends toward the saw blade assembly 60. This may facilitate engagement between the displacement sensing arm 412 and the bushing 454 of the saw blade assembly 60. As shown, in FIGS. 8A-8B and 9, the distal portion 414 may be an at least partially arcuate member extending along a radius of curvature toward the saw blade assembly 60. However, the distal portion 414 may be shaped differently (e.g., the distal portion 414 may be a linear portion extending at an angle or perpendicularly from the proximal 418 toward the saw blade assembly 60).

The saw blade assembly 60 may include a shank that is disposed adjacent to a proximal end of the assembly 60. Furthermore, the assembly 60 may include a cutting edge at the distal end thereof. The cutting edge may include a cutting edge that, when oscillated serves to cut the medium into which the blade 16 is advanced as per a standard saw blade. The direction in which the saw blade is advanced during a cutting operation may be referred to as a cutting direction 120 that is generally orthogonal to the cutting edge. A blade member may extend between the shank and the cutting edge. The cutting edge, body, and shank may collectively define the saw blade 16.

In addition to the saw blade 16, the saw blade assembly 60 may also include a bushing 452 as referenced above. The bushing 452 may engage the blade member to facilitate relative movement of the bushing 452 relative to the blade member along a direction corresponding to the cutting direction 120. For example, the bushing 452 may include an aperture through which at least a portion of the blade member may be disposed. The aperture may form an opening that extends at least in a direction corresponding to the cutting direction 120 of the saw blade 16. The opening may be sized to receive the blade member therein such relative movement between the opening and the blade member is provided. As such, the saw blade 16 may be free to oscillate within the aperture, and the bushing 452 may slideably engage the member for relative movement therebetween that is constrained along the direction corresponding to the cutting direction 120.

Figure 10:
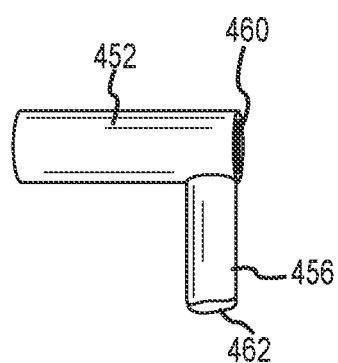
FIG. 10 is an elevation view of an embodiment of a bushing for a saw blade penetration measurement system.

The bushing 452 may include an engagement member that is disposed on the bushing 452 and adapted for engagement with a displacement sensing arm 412 of a saw 50 to which the saw blade assembly 60 is engaged. For instance, the engagement member may include a post 456 extending from the bushing 452 (FIG. 10). The post may extend away from the cutting direction 120 of the saw blade assembly 60. In an embodiment, the post may extend perpendicularly to the cutting direction 120. Accordingly, the post may engage a hole provided on the distal portion of the displacement sensing arm 412. In this regard, the post may extend into the hole. Movement of the bushing 452 relative to the saw blade 16 in a direction corresponding to the cutting direction 120 may result in the post acting on the hole such that the displacement sensing arm 412 undergoes corresponding movement upon movement of the bushing 452 relative to the saw blade 16. In turn, as described above, the core at the proximal portion the displacement sensing arm 412 may also undergo corresponding movement relative to the coil 416, which may be detected by the displacement sensor 410 and output as a displacement measure.

It may be appreciated that other arrangements for engaging the bushing 452 with the displacement sensing arm 412 may be provided so that the bushing 452 and displacement sending arm 412 undergo corresponding movement. For example, other structures such as clasps, fasteners, or other mechanisms may be utilized to engage the bushing 452 to the displacement sensing arm 412. Furthermore, the bushing 452 may, in some embodiments, be integrally defined on the distal portion 414 of the displacement sensing arm 412. In this regard, a standard saw blade 16 may be engaged with a chuck 420 of the saw 50 and the bushing 452 may be disposed relative to the blade 16. In any regard, the bushing 452 may be pivotal relative to the displacement sensing arm 412 (e.g., in a direction perpendicular to the cutting direction 120) to facilitate ease of engagement of the bushing 452 with the displacement sensing arm 412 or the bushing 452 with the saw blade 16 when engaging the saw blade 16 with the chuck 420 of the saw 50.

Figure 14:
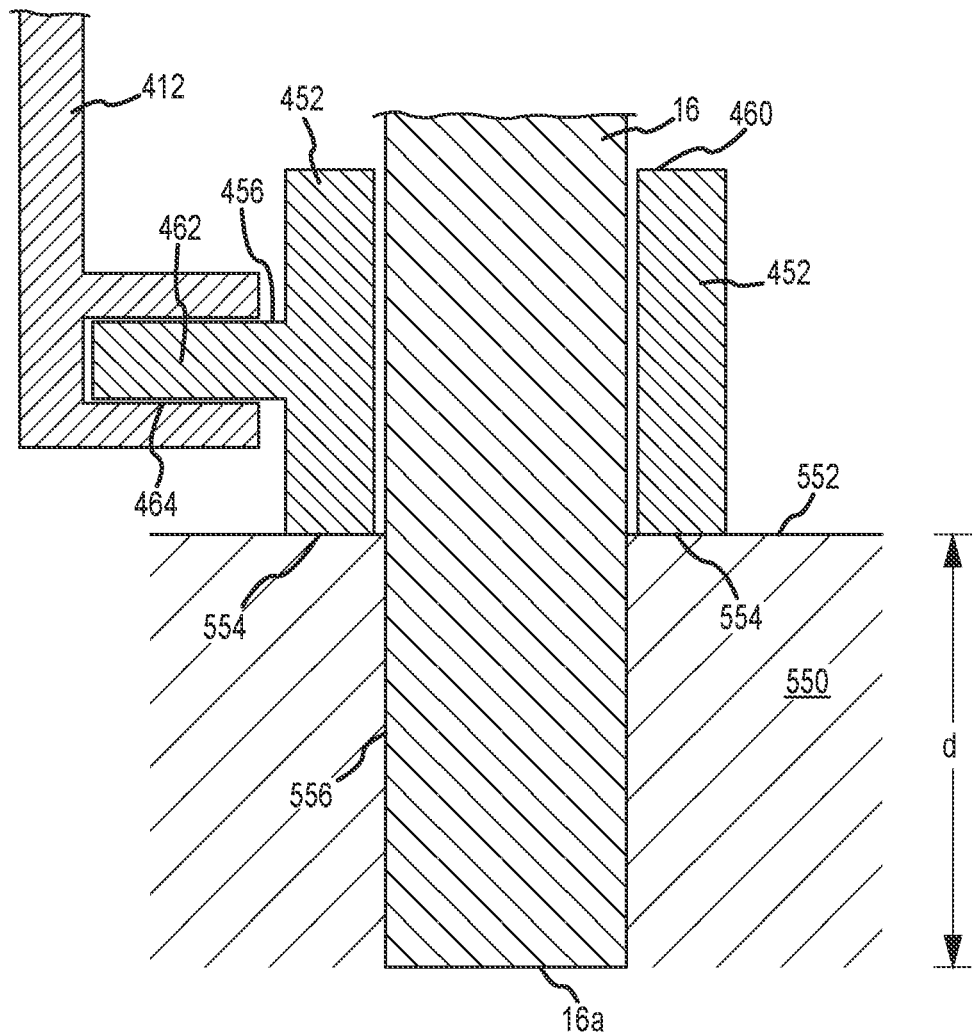
FIG. 14 is a cross sectional schematic view of a saw blade that has been advanced into a cut in a medium relative to a bushing engaged with a distal portion of a displacement sensing arm.

For instance, with further reference to FIG. 14, a schematic section view of a saw blade 16 that has been advanced into a medium 550 is shown. The bushing 452 may be disposed about the saw blade 16. As such, the bushing 452 may be disposed about the periphery of the cut 556 created upon advancement of the saw blade 16 into the medium 550. That is, the bushing 452 may remain in contact with the surface 552 of the medium 550 upon advancement of the saw blade 16 into the medium 550. In this regard, the bushing 454 may include a reference surface 554 at a distal portion thereof. The reference surface 554 may contact the surface 552 of the medium 550 to be sawed. As such, prior to initiation of the sawing when the cutting edge 16a of the saw blade 16 is also in contact with the surface 552, the displacement sensor 410 may be set to establish the reference point. Accordingly, as the saw blade 16 is advanced, the reference surface 554 may remain in contact with the surface 552 of the medium 550. The reference surface 554 may contact the surface 552 about a periphery of the cut 556. In an embodiment, the reference surface 554 may extend about a majority or substantially all of the saw blade 16 such that the reference surface 554 may also extend about a majority of or substantially all of the periphery of the cut 556. The distally biased displacement sensing arm 412 may act on the bushing 452 (e.g., by way of post 462 received in hole 464) to maintain the bushing 452 in contact with the surface 552. In any regard, the displacement (d) of the cutting edge 16a of the saw blade 16 relative to the reference surface 554 of the bushing 454 may be measured upon corresponding movement of the core 422 at the proximal end 418 of the displacement sensing arm 412 relative to the coil 416.

In this regard, measurement of the displacement of the cutting edge 16a of the saw blade 16 relative to the reference surface 554 of the bushing 454 that is maintained against the surface 552 of the medium 550 to be sawed may provide improved accuracy regarding the displacement of the cutting edge 16a into the cut 556. As described above, as the reference surface 554 is maintained in contact with the medium 550 adjacent to the periphery of the cut 556, there is less possibility for relative movement between the bushing 452 and the medium 550 that may introduce error into the measured displacement d. Furthermore, as the bushing 452 is in contact with the medium 550 adjacent to the cut 556, the contact with the patient required to obtain the measurement is lessened as the extension 110 may not need to contact the patient in a location away from the cut 556. Thus, the sawing operation is less invasive, thus improving patient outcomes.

A number of additional features may also be provided for the saw 50 and/or saw blade assembly 60 that are described in conjunction with the embodiment of the saw 50. It may be appreciated that these features may be provided with other types of saws and/or saw blade assemblies 60 and are not required to be used in conjunction with a saw 50 and saw blade assembly 60 incorporating features for coordinated operation between the displacement sensor 410 and saw blade assembly 60 as described above.

Figure 11:
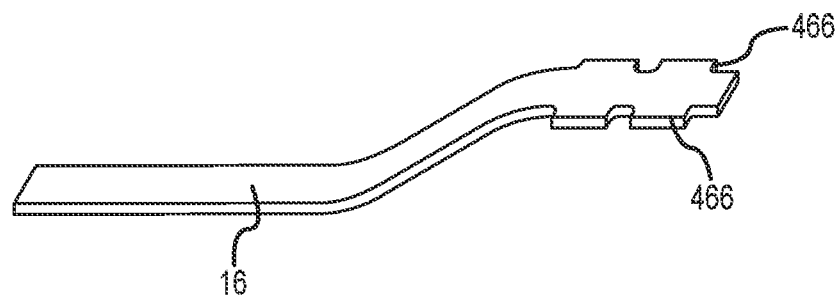
FIG. 11 a perspective view of an embodiment of a saw blade with an intact destructible portion.
Figure 12:
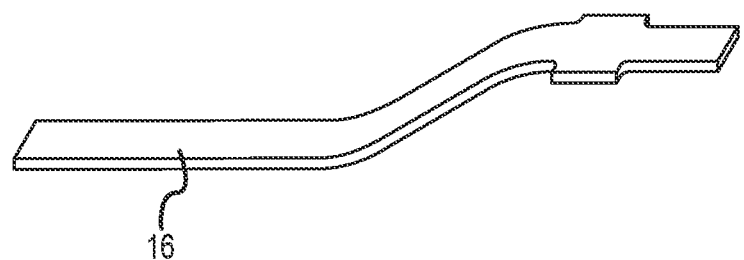
FIG. 12 is a perspective view of the embodiment of the saw blade of FIG. 11, wherein the destructible portion has been at least partially destroyed.

For instance, as may be further appreciated with reference to FIGS. 11 and 12, a saw blade 16 may incorporate features that prevent reuse of the saw blade 16. In this regard, surgical saw blades are often employed as single use items such that the blades are specifically designed to be used for a single procedure or portion thereof and disposed after use rather than being reused. There are several rationales for doing so, including the safety of the patient to ensure that the saw blade 16 to be used in a procedure has not been worn or damaged by use in previous procedures. In this regard, the features described below may help prevent the saw blade 16 from being reused. As may be appreciated, the saw blade 16 disclosed in this respect may be used in a saw blade assembly 60 as described above.

Specifically, the saw blade 16 may include a destructible portion 466 of the shank. The destructible portion 466 may be degraded or destroyed when exposed to common cleaning procedures to which surgical instruments are routinely exposed. Upon destruction of the destructible portion 466, the shape of the shank may be altered. The altered shape of the shank may result in a reduced ability to engage the saw blade 16 with a chuck 420. Such cleaning procedures may include exposure to steam cleaning at elevated heat and/or pressure in an autoclave process or may include exposure to cleaning chemicals or the like. In this regard, when, for example, the destructible portion 466 is exposed to temperatures associated with cleaning in an autoclave, the destructible portion 466 may be degraded or destroyed (e.g., by melting or other degradation due to heat) to prevent reuse of the saw blade assembly 60. Accordingly, in an embodiment, the melting temperature of the destructible portion may be greater than an operating temperature (e.g., substantially similar to room temperature or 22.3° C.+/−20° C.). Accordingly, in an embodiment, the melting temperature may be not less than about 50° C. and not greater than about 130° C. In an embodiment, the melting temperature of the destructible portion may be not less than about 60° C. and not greater than about 110° C.

While autoclave cleaning is a common method of sterilization and cleaning of instruments between procedures, it may be appreciated that other methods of cleaning may be employed. As such, the destructible portion 466 may be adapted to be degraded or destroyed during such cleaning procedures. For example, the destructible portion 466 could alternatively or additional be adapted to be degraded or destroyed upon exposure to a cleaning element such as a cleaning chemical or the like. In any regard, upon an attempt to sterilize or otherwise clean the saw blade assembly 60 for reuse, the destructible portion 466 may be destroyed or degraded to the point of eliminating the effectiveness of the saw blade assembly 60 to prevent reuse of the saw blade assembly 60.

With further reference to FIG. 11, one particular embodiment of a saw blade assembly 60 including a destructible portion 466 is shown where the destructible portion may include a portion of the shank of the saw blade assembly 60. As shown, the destructible portion 466 includes a proximal end of the shank. As such, at least a portion of a sidewall and/or an endwall of the shank may be defined by the destructible portion 466. As may be appreciated, the shank sidewall and endwall may be adapted for engagement with the chuck such that the chuck contacts the sidewalls and endwall (or tabs) upon engagement with the shank.

For instance, the chuck may include a correspondingly-shaped opening that is sized to have corresponding sidewalls that may contact the tabs when the shank is received in the chuck. As such, upon receipt of the shank in the chuck, the chuck may define a bearing surface interface that allows the chuck to impart an oscillating motion to the saw blade 16.

Accordingly, when, as shown in FIG. 12, the destructible portion 466 is destroyed or degraded and may be removed. The result may be at least a lack of registration of the shank relative to the chuck. This may prohibit the ability of the saw blade assembly 60 to be used because the lack of registration may prevent the saw blade 16 from properly turning so as to at least inhibit the use of the saw blade assembly 60 in a procedure. Additionally or alternatively, the destructible portion 466 may be degraded to the point where the shank is no longer receivable by the chuck (or other attachment device).

As may also be appreciated in FIGS. 11 and 12, the shank may include chuck engagement features that may be engaged by the chuck to retain the saw blade assembly 60 relative to the chuck. For instance, the chuck may include retention pins that are biased to extend into the chuck opening in an engaged position to engage detents of the shank.

Furthermore, the saw 50 may include a removable chuck 420 that provides for quick interchange and/or removal of the chuck. As may further be appreciated from FIG. 9, the saw 50 may include a drive having a motor 432 and gearbox 434. The drive 430 may engage a chuck 420. Specifically, the chuck 420 may be provided in removable engagement with the drive 430 such that the chuck 420 may be releasably engaged with the drive 420. The chuck 454 may include a chuck drive coupling at a proximal end thereof. In this regard, the saw 50 may include a corresponding saw drive coupling that engages with the chuck drive coupling to impart oscillating motion from the drive 430 to the chuck 420. In this regard, the chuck 420 may be detachable from the saw 50.

As may be appreciated, when sawing using the saw 50, a second sensor for measurement of force acting on the cutting edge 16a of the saw blade 16 may also be provided. In this regard, a second sensor 118' (e.g., a force sensor such as piezoelectric crystal) may be disposed proximally to the saw drive 430. In turn, force acting on the cutting edge 16a of the saw blade 16 as it is advanced in the sawing process may be transferred to the second sensor 118' via the saw drive 430. That is, the force acting on the cutting edge 16a of the saw blade 16 may be transferred through the shank of the blade 16 to the chuck 420, and the saw drive 420. In turn, the drive 430 may act upon the second sensor 118' to produce an output corresponding to the force acting on the cutting edge 16a. In this regard, it may be appreciated that the rigid assembly of the saw drive 430, chuck 420, and saw blade 16 may transmit the force acting on the cutting edge 16a of the saw blade 16 to the second sensor 118. It may further be appreciated that the saw drive 430 may be fixed relative to the saw housing 26 so as to impart oscillation to the chuck 420. At least a majority of the force acting on the cutting edge 16a of the saw blade 16 may be transferred to the second sensor 118. In an embodiment, the second sensor 118 may have a range of measureable force from about 0 lbf (0 N) to about 100 lbf (445 N). In an embodiment, the second sensor 118 may have a range of measurable force from about 0 lbf (0 N) to about 25 lbf (111 N). The second sensor 118 may have a precision of at least about 1% of the maximum measureable force. Accordingly, in an embodiment, the second sensor may have a precision of at least about 0.25 lbf (1.1 N). In an embodiment, the second sensor 118 may have a precision of 0.5% (e.g., about 0.125 lbf (0.56 N) in an embodiment).

In this regard, the saw drive 430, as shown best in FIG. 9, may be mounted to the saw housing 26 by way of a suspension member 494. The suspension member 494 may be operatively engaged to the saw housing 26 and the saw drive 430 so as to maintain the saw drive 430 stationary to transfer force acting on the cutting edge 16a of the saw blade 16 to the second sensor 118. As such, the suspension member 494 may be supportively engaged to the saw drive 430 at a first end of the suspension member 494. The suspension member 494 may also be affixed to the saw housing 26. The suspension member 494 may allow for linear movement along the cutting direction 120. In this regard, the suspension member 494 may comprise a spring member that allows for motion relative to the direction along the cutting direction 120. The spring member may have a spring coefficient slight enough relative to the direction corresponding to the cutting direction 120 such that the force resulting from displacement of the suspension member 494 may be insignificant (e.g., less than about 1%, less than about 0.5% or even less than about 0.1%) of the force applied to the cutting edge 16a of the saw blade 16 during the sawing operation.

Figure 15B:
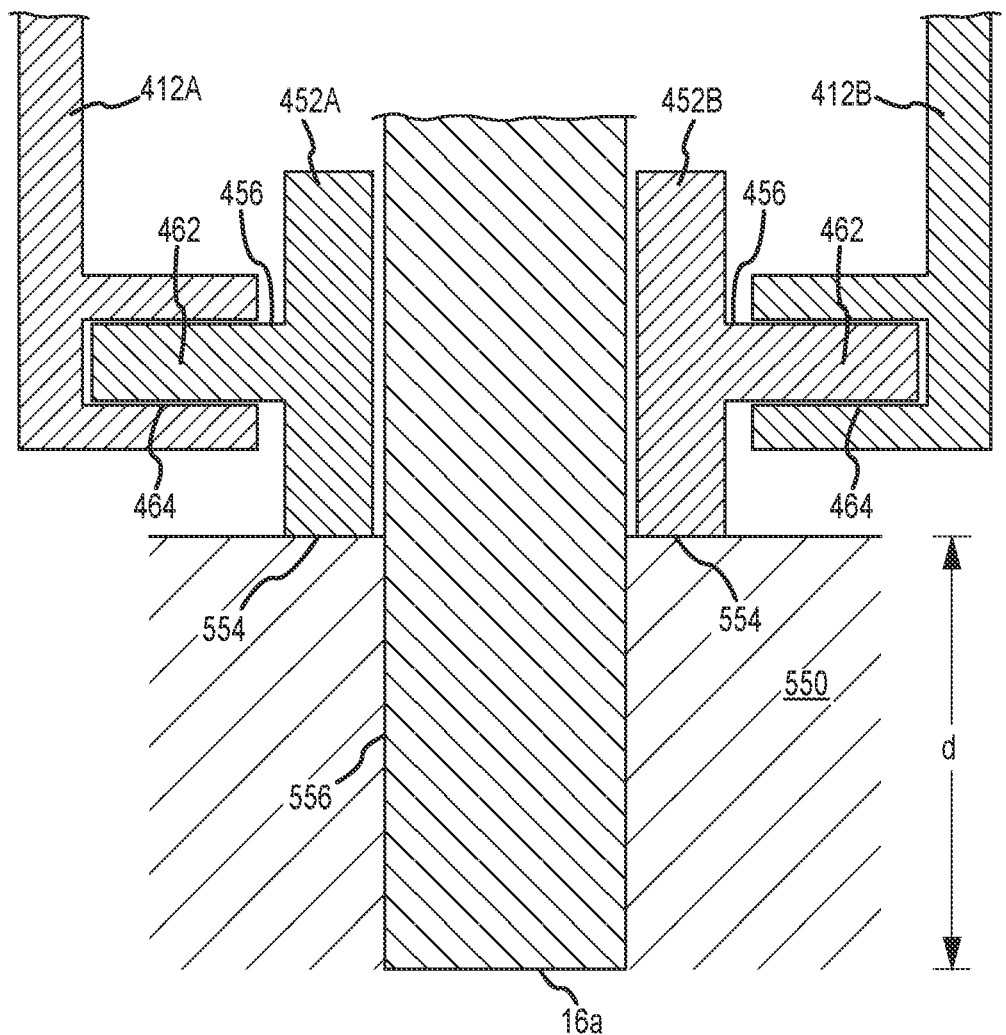
FIGS. 15B and 15C are cross sectional schematic views of the saw blade from FIG. 15A that has been advanced into a cut in a medium relative to two bushings engaged with a distal portion of respective displacement sensing arms.
Figure 15C:
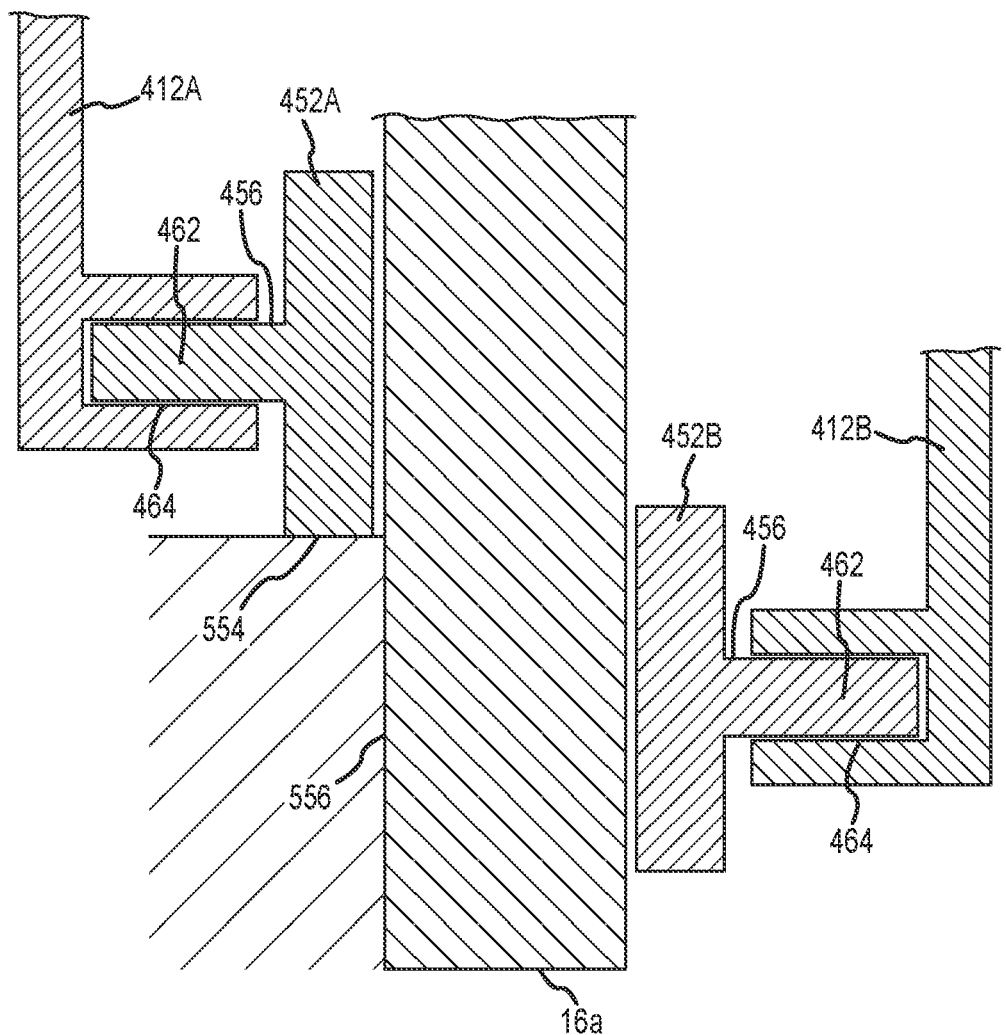

As shown in FIGS. 15A-C, an embodiment of a saw 50A with two measurement systems is shown. Displacement sensors similar to the displacement sensor 410 of FIG. 9 may be integrated into a housing of the saw 50A. In this regard, the displacement sensors may each include a depth sensing arm 412A, B that is specifically adapted for engagement with a bushing 452A, B. In this regard, the depth sensing arms 412A, B may be used to establish reference points from which displacement of the saw blade 16 may be measured as described above.

The displacement sensors may include a depth sensing arm 412A, B that may extend from the saw housing. For example, the depth sensing arm 412A, B may extend distally (e.g., from a distal face 30 of the saw housing) in a direction corresponding with the direction in which the saw blade 16 extends from a chuck of the saw 50A. At least a portion of the displacement sensing arms 412A, B may extend from the saw housing along the length of the saw blade 16 of the saw 50A. The depth sensing arms 412A, B may also include a distal portion 414 that is adapted to engage a bushing 452A, B. As used herein, distal may correspond to a direction from the saw 50A toward the cutting edge of the saw blade 16 and proximal may correspond to a direction from the cutting edge of the saw blade 16 toward the saw 50A. In this regard, at least a portion of the depth sensing arms 412A, B (e.g., the distal portion 414) may be adapted to engage the bushings 452A, B of the saw blade assembly. In any regard, at least a portion of the depth sensing arms 412A, B may extend into the housing. The housing of the saw 50A may contain components for both of the sensing arms 412A, B that are shown within the housing 26 of FIG. 9. As such, a proximal end of the displacement sensing arm 412B also interfaces with a coil of a displacement sensor that may be disposed within the saw housing.

FIG. 15C shows when the cut has been completed and one side of the medium 550 has been dislodged. This causes one of the bushings 452B to release due to a lack of counter force from the medium 550. When this occurs the processor will receive a signal from the position sensor associated with the second bushing 452B that is quite different from a signal from the position sensor associated with the first bushing 452A. In one embodiment, the processor will generate a signal indicating that the cut is complete when the signals from the two position sensors differ by greater than a previously defined threshold amount. This generated signal causes an automatic slowing of motion or stopping altogether of the saw motor. An output device may generate an alert (visual, tactile or audible) for a saw user based on the generated cut completion signal.

Figure 16:
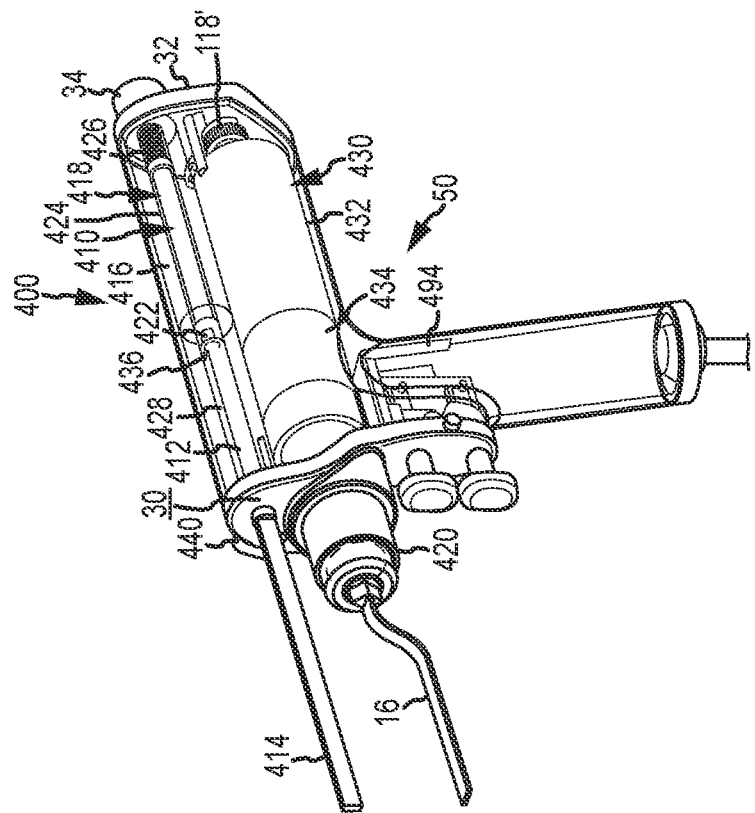
FIG. 16 is a perspective view with a partial cutaway of a sawing assembly of an embodiment of a saw including a saw blade penetration measurement system and a cutting board/cutting jig.

FIG. 16 shows the saw 50 used with an exemplary cutting guide/jig 480. In one embodiment, the cutting guide/jig 480 is U-shaped for receiving a portion of a patient's anatomy. The cutting guide/jig 480 includes two opposing walls. The walls include slot guides 482 that receive the saw blade 16. The slot guides 482 can be thin enough to act as bearing members to the received saw blade 16 without cause undue friction during oscillation of the saw blade. As the saw blade 16 is received within the slot guides 482 a displacement sensing arm 412 uses the side of the cutting guide/jig 480 as a reference surface. Thus, the cutting block 480 may receive the saw blade in the slot guides 482 to direct the saw blade relative to the patient's anatomy. The displacement sensing arm 412 and related components (processor) generate a cutting depth value that takes into consideration the thickness of the wall of the cutting guide/jig 480—provided the item being cut maintains contact with the interior wall of the cutting guide/jig 480. Furthermore, the displacement sensing arm 412 may contact a portion of the cutting block 480 that is stationary relative to the anatomy to be cut rather than the anatomy itself.

In one embodiment, the cutting guide/jig 480 is adjustable for allowing different sized patient parts to be received. Also, the height, depth and width of the slot guides 482 is also adjustable for accepting different size and time type of cutting blades (e.g., reciprocating, ultrasonic, etc.) Also, guide(s) separate from or attachable to the cutting guide/jig 480 provide barriers for guiding motion of the housing of the saw in a desired cutting direction.

Figure 17A:
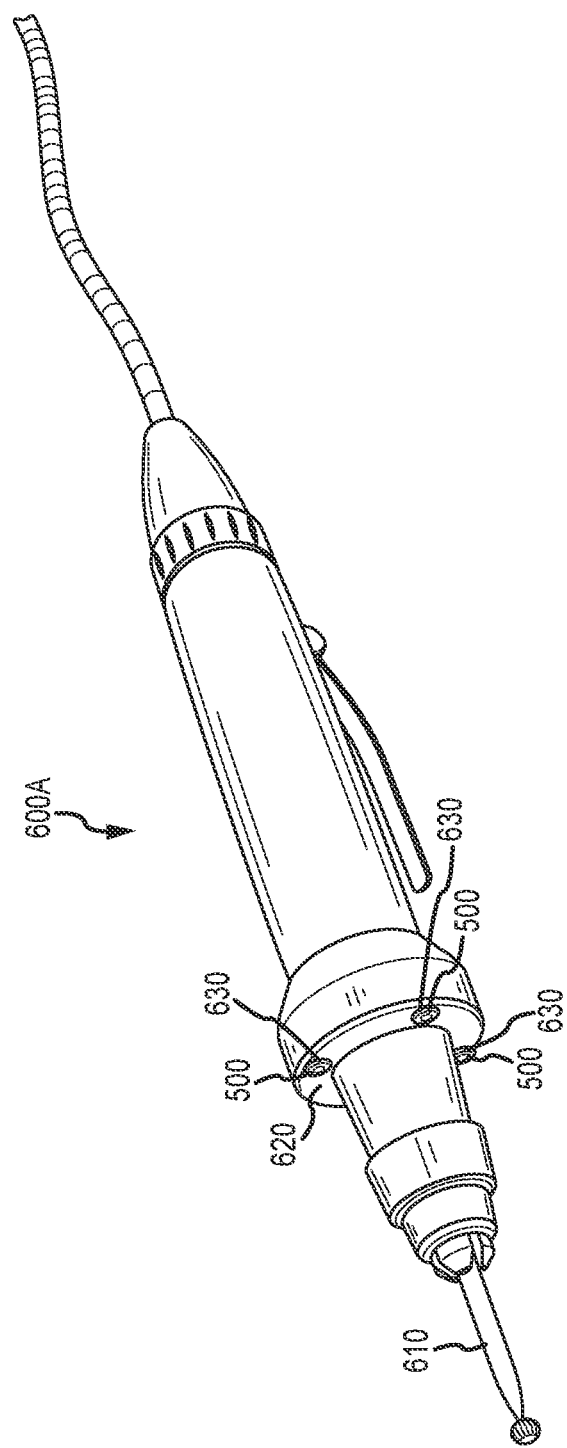
FIGS. 17A-17C depict various embodiments of surgical instruments including light emitters.
Figure 17B:
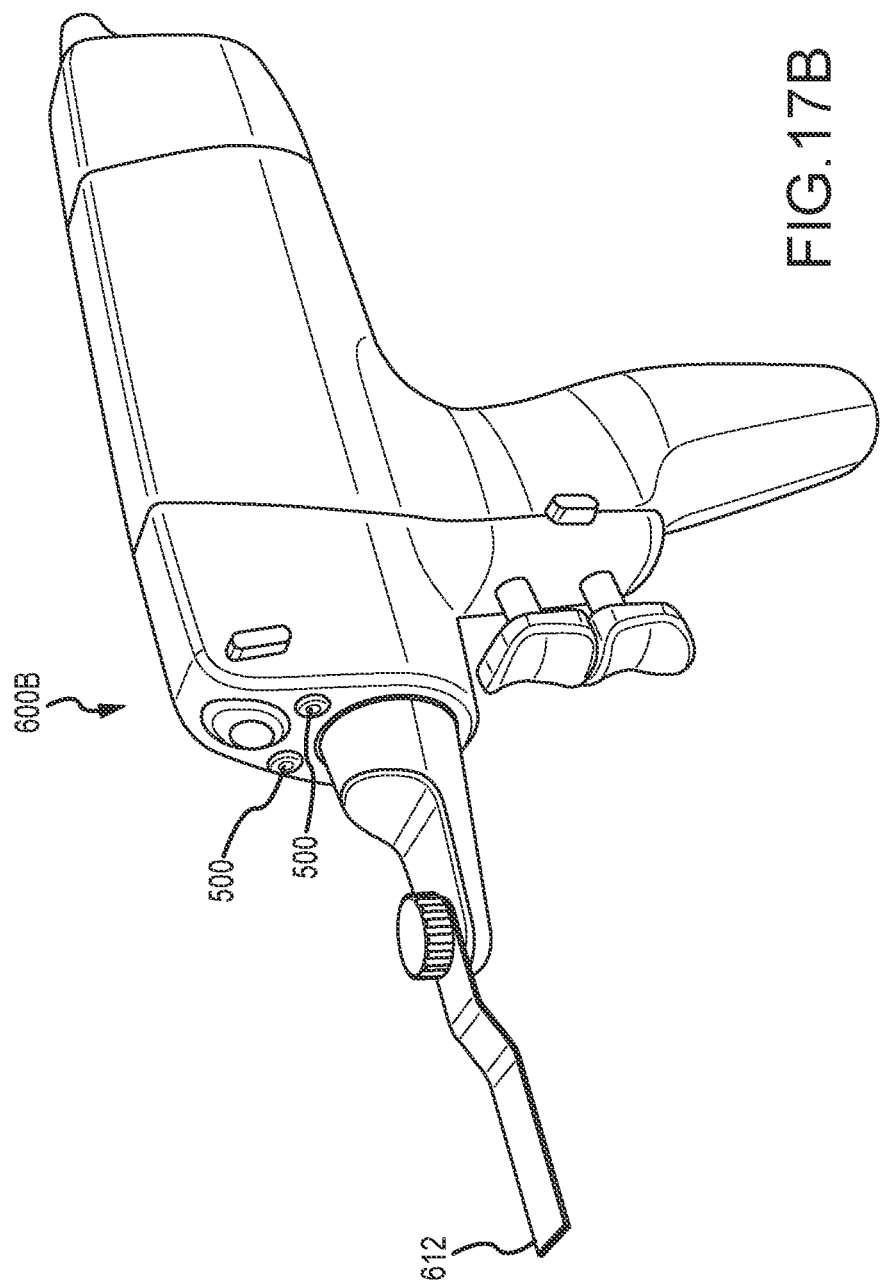
Figure 17C:
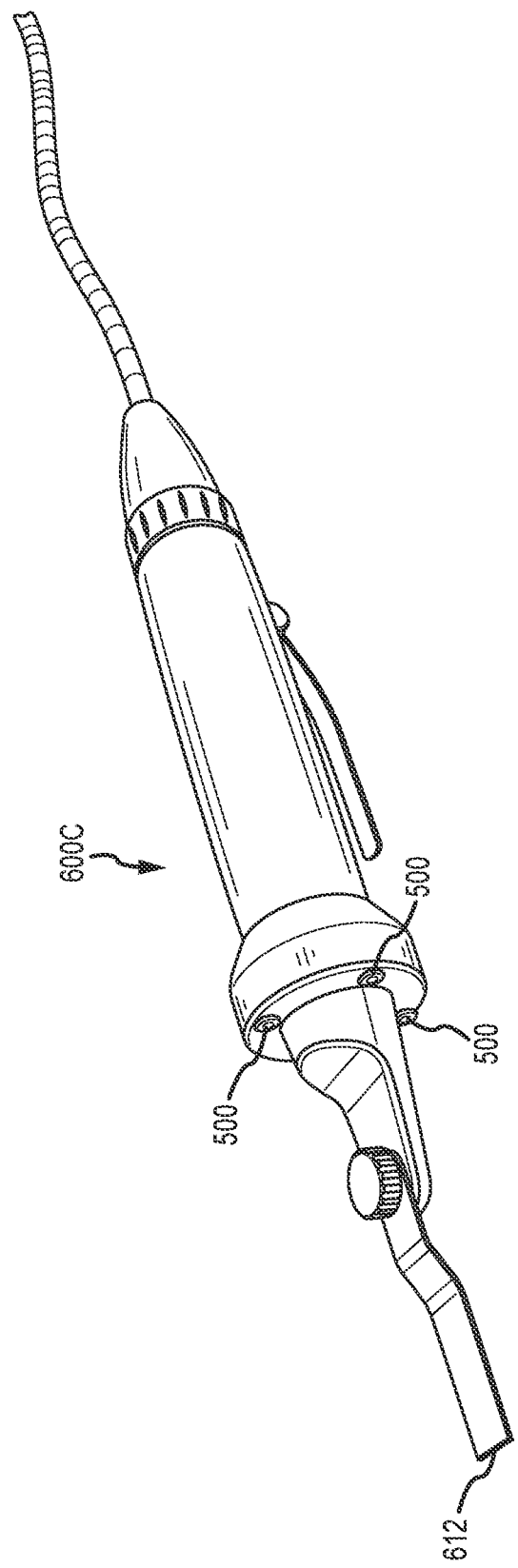
Figure 18:
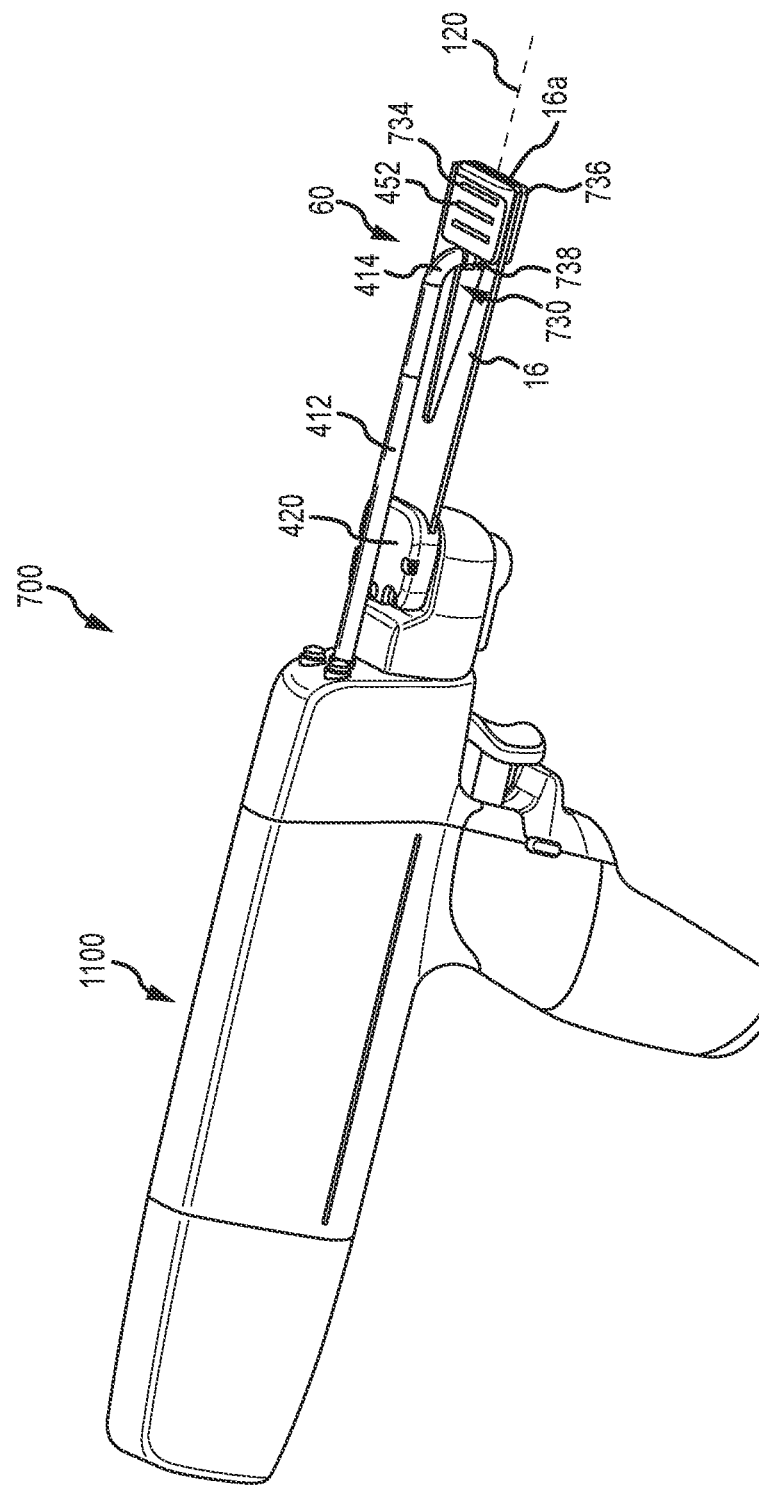
FIG. 18 is a perspective view of an embodiment of a saw including a saw blade penetration measurement system.

As shown in FIGS. 17A-C, the saw may also include a light emitter 500 disposed on a distal face 30 of the saw housing 26. In this regard, the light emitter 500 may be operable to emit light in a direction toward the saw blade 16 when engaged with the chuck 420. As such, the light emitter 500 may illuminate at least a portion of the saw blade 16 during the sawing operation to improve visibility of the medium being sawed. The light emitter 500 may include a light source such as, for example, an incandescent bulb, a light emitting diode (LED), a laser source, or other light source known in the art. Alternatively, a light source may be disposed remotely from the light emitter 500 and the light may be transmitted from the remote light source to the light emitter 500 using optical elements such as fiber optics or the like. It may further be appreciated that a light emitter 500 like the one shown in the accompanying figures may be provided with other types of surgical instruments without limitations. For example, a light emitter 500 of the type described herein may be provided with other types of saws, saws, or other surgical tools. Accordingly, the light emitter 500 may be appropriately disposed relative to the surgical field so as to direct light from the light emitter 500 toward the interface of the surgical tool with the portion of the surgical field contacted by the surgical tool.

The light emitter 500 may be selectively operated or may be operated when the saw 50 is operated. In this regard, the light emitter 500 may be selectively toggled on and off or may include different levels of intensity. The selector for the light emitter 500 may be at the controller housing 146 (e.g., a selectable option on the display 152). The light emitter 500 may also be activated upon activation of the saw 50. Additionally, the operation of the light emitter 500 may be selectable between operation with the saw 500 and selective toggling of the light emitter 500.

In a further embodiment, the light emitter 500 may be adapted for use with any appropriate surgical instrument. In this regard, further examples of surgical instruments are shown in FIGS. 17A-C, respectively. For example, in FIG. 17A, a burr grinder 600A is shown, in FIG. 17B, a second sagittal saw 600B is shown with a first grip embodiment, and in FIG. 17C, a third sagittal saw 600C is shown with a second grip embodiment. In FIG. 17A, the burr grinder 600A may include an instrument working portion comprising a rotatable burr grinding bit 610. In this regard, the burr grinding bit 610 may be contactable with the patient to perform a grinding operation. The burr grinder 600A may also include one or more light emitters 500. As may be appreciated, the light emitters 500 may be disposed on a distal face 620 of the burr grinder 600A such that the light emitters 500 may be operable to emit light in a direction toward the patient when the burr grinding bit 610 is in contact with the patient. That is, the light emitter 500 may act to illuminate a surgical field in which the burr grinder 600A is employed. In the case of a plurality of light emitters 500, the light emitters may be spaced equally about a portion of the distal face 620 surrounding the working portion of the burr grinder 600A. The light emitters 500 may be disposed within a housing of the burr grinder 600A such that the light emitters 500 may be protected from environmental elements (e.g., fluid or the like) that may be present when the burr grinder 600A is in use. As such, the light emitters 500 may include or be disposed behind a transparent or translucent shield 630 that may protect the light emitters 500 and/or light source associated with the light emitters 500 from such environmental elements. The light emitters 500 shown in FIG. 17A may be operated according to any of the foregoing discussion regarding the light emitters 500 described above.

Furthermore, with further reference to FIGS. 17B and 17C, it may be appreciated that the light emitters 500 may be provided in connection with other surgical instruments. For instance, in FIG. 17B, a sagittal saw 600B with a first grip embodiment (i.e., a pistol grip style grip) is shown. In this regard, it may be appreciated that a sagittal saw blade 612 may be provided as the working portion of the sagittal saw 600B. As such, the sagittal saw blade 612 may be reciprocated such that contact of the distal portion of the sagittal saw blade 612 may act to cut anatomy of the patient. As such, the light emitters 500 may be disposed on a distal face of the sagittal saw 600B such that the light emitters 500 may emit light toward the patient when the sagittal saw blade 612 contacts the patient in a cutting operation. Further still, FIG. 17C shows another embodiment of a sagittal saw 600C with a second grip embodiment. As may be appreciated, the light emitters 500 of the sagittal saw 600C may be disposed about the sagittal saw blade 612 in a manner as described above with respect to the burr grinder 600A.

Figure 19:
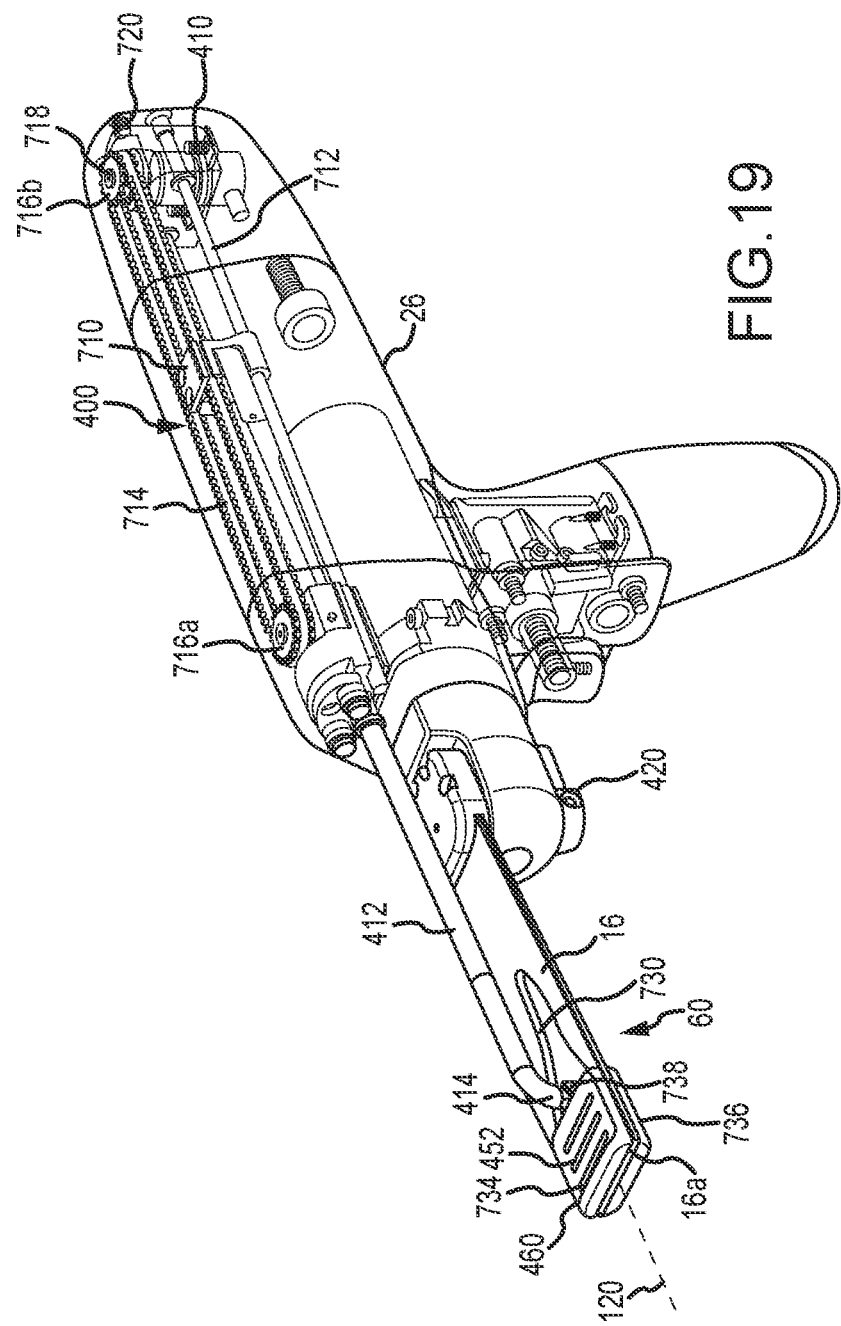
FIG. 19 is a perspective view of the embodiment of FIG. 18 in partial cutaway view to expose internal components of the embodiment of the saw for illustrative purposes.
Figure 20:
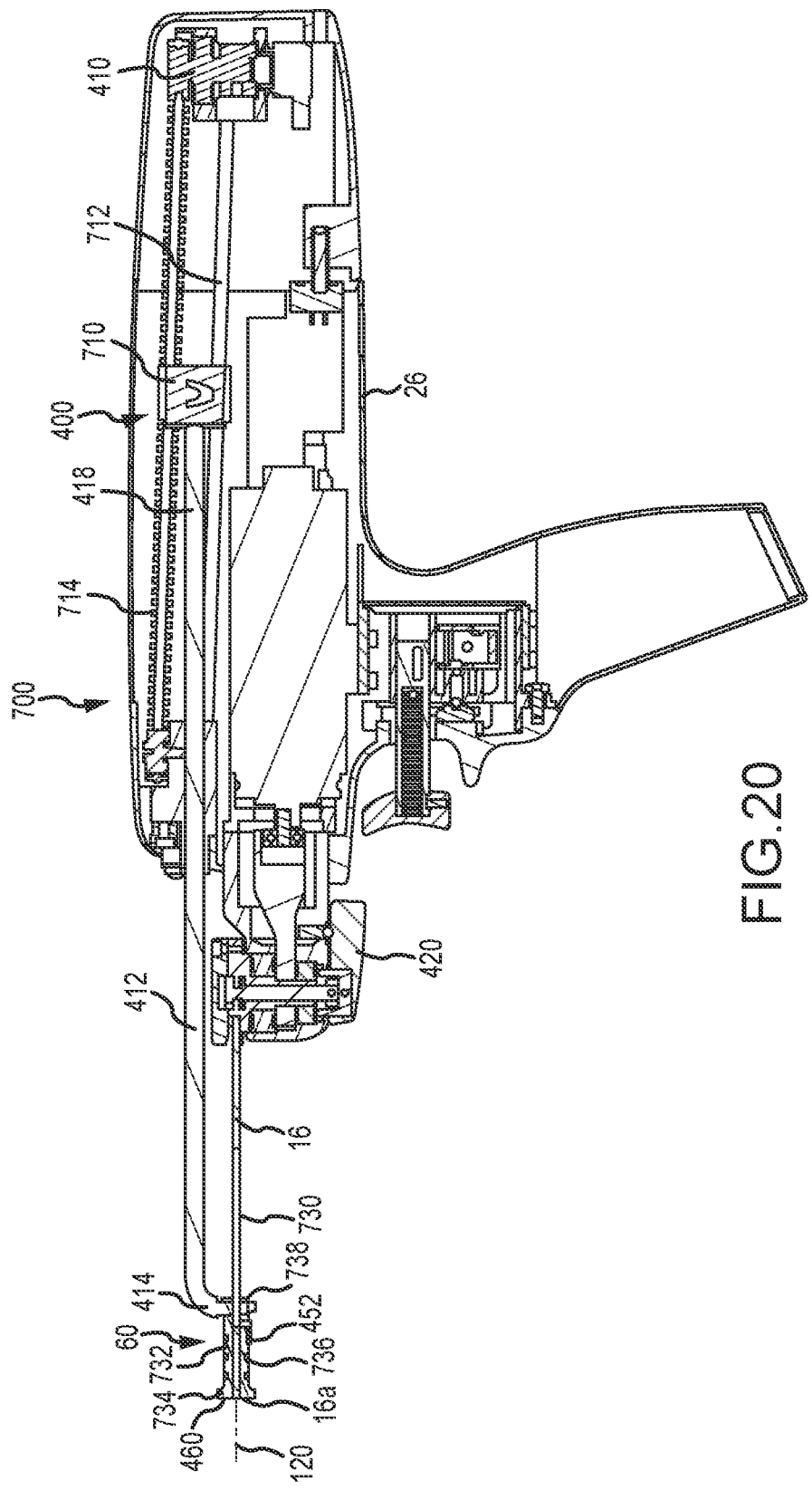
FIG. 20 is a cross-sectional view of the saw FIG. 18.

With further reference to FIGS. 18-21C, an embodiment of a saw 700 that may also include a measurement system 400 for the measurement of the displacement of the leading edge 16a of the saw blade 16 when advanced into a medium. In this regard, the saw 700 may include a displacement sensing arm 412 that extends from a saw housing 26 in a manner similar to that described above. With further reference to FIGS. 19 and 20, both of which depict internal components disposed within the saw housing 26, the saw 700 may include a displacement sensor 410. Specifically, the displacement sensor 410 may be a digital encoder 720 that is operative to output a signal representative of the displacement of the displacement sensing arm 412 with respect to the leading edge 16a of the saw blade 16.

In this regard, the proximal end 418 of the displacement sensing arm 412 may extend into the housing 26 of the drill 700. Specifically, the proximal end 418 of the displacement sensing arm 412 may contact a shuttle 710 that is slideably engaged with a plurality of rails 712 extending in a direction parallel to the cutting direction 120 of the saw blade 16. The shuttle 710 may further be engaged with a belt 714. The belt 714 may be disposed about a plurality of gear hubs 716a and 716b. In this regard, the shuttle 710 may engage a point on the belt 714 such that as the shuttle 710 moves in sliding engagement along the rails 712, the belt 714 imparts rotational motion to the gear hubs 716a and 716b.

The gear hub 716b may be fixed on a shaft 718 that extends into the digital encoder 720. In this regard, rotation of the shaft 718 may be sensed by the digital encoder 720 and transformed into a corresponding displacement signal associated with the movement of the shuttle 710 when moved by the displacement sensing arm 412. The shuttle 710 may be biased to a distal position.

Furthermore, the distal portion 414 of the displacement sensing arm 412 may engage a bushing 452 as described above. In this regard, the bushing 452 may be engaged with the saw blade 16. Specifically, the bushing 452 may include a post 732 extending through an aperture 730 in the saw blade 16. Specifically, the post 732 may extend between a first portion 734 of the bushing 452 on a first side of the saw blade 16 and the second portion 736 of the bushing 452 on a second side of the saw blade 16 opposite the first side of the saw blade 16. In this regard, the bushing 452 may be captive relative to the saw blade 16 such that the bushing 452 may move with respect to the confines of the aperture 730 as the post 732 may constrain the bushing 452 within the aperture 730. The bushing 452 may include an engagement portion 738 that engages the distal portion 414 of the displacement sensing arm 412. Specifically, the engagement portion 738 may comprise a snap interface such that the engagement portion 738 snaps onto and is engageable with the distal portion 414 corresponding movement therewith. Thus, as may be appreciated, the bushing 452 may include a reference surface for 60 that is alignable with the distal edge 16a to define a reference point relative to the distal edge 16 a is described above.

Furthermore, it may be appreciated that the aperture 730 in the saw blade 16 may generally be tapered or fan shaped such that the aperture extends across the greater lateral extent of the saw blade 16 towards the distal end thereof and converges to a lesser lateral extent of the saw blade 16 as the aperture extends proximally. This may be provided to account for the greater reciprocal distance traveled by the saw blade at the distal end thereof such that as the bushing 452 moved relative to the saw blade 16 in a proximal direction, the corresponding relative movement between the bushing 452 and saw blade 16 may be reduced given the relatively shorter stroke of the oscillations of the saw blade 16 at a proximal location.

In any regard, the bushing 452, once engaged with the displacement sensing arm 412 may undergo corresponding relative movement therewith. As such, when the saw blade 16 is advanced into a medium, the reference edge 460 of the bushing 452 may move relative to the leading edge 16 a of the saw blade as the saw blade 16 is advanced during a sawing operation as described above. In turn, the relative movement between the bushing 452 and the leading edge of the saw blade 16a may be detected by the digital encoder 720 as the displacement sensing arm 412 displaces the shuttle 710 along the rails 712, thus turning the belt 714 on the gear hubs 716a and 716b that is detectable by the digital encoder 720.

Figure 21A:
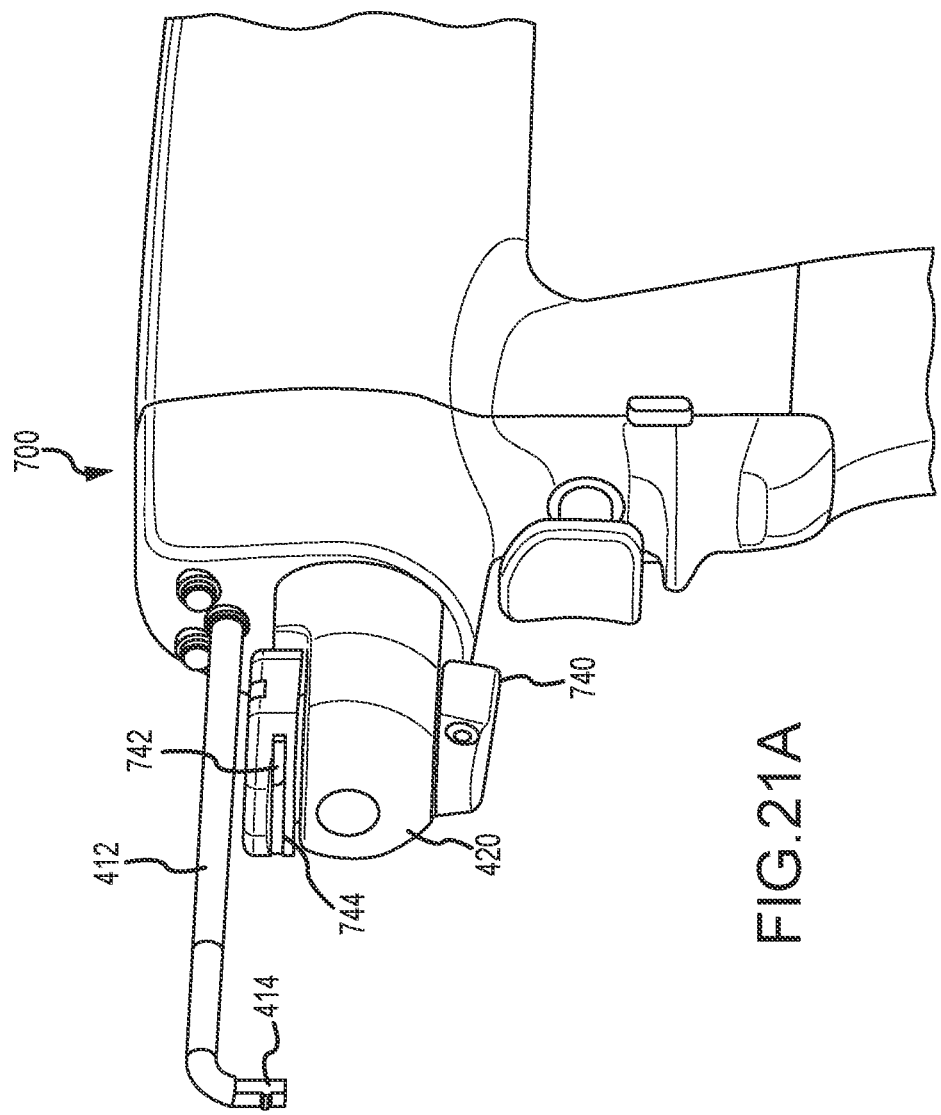
Figure 21B:
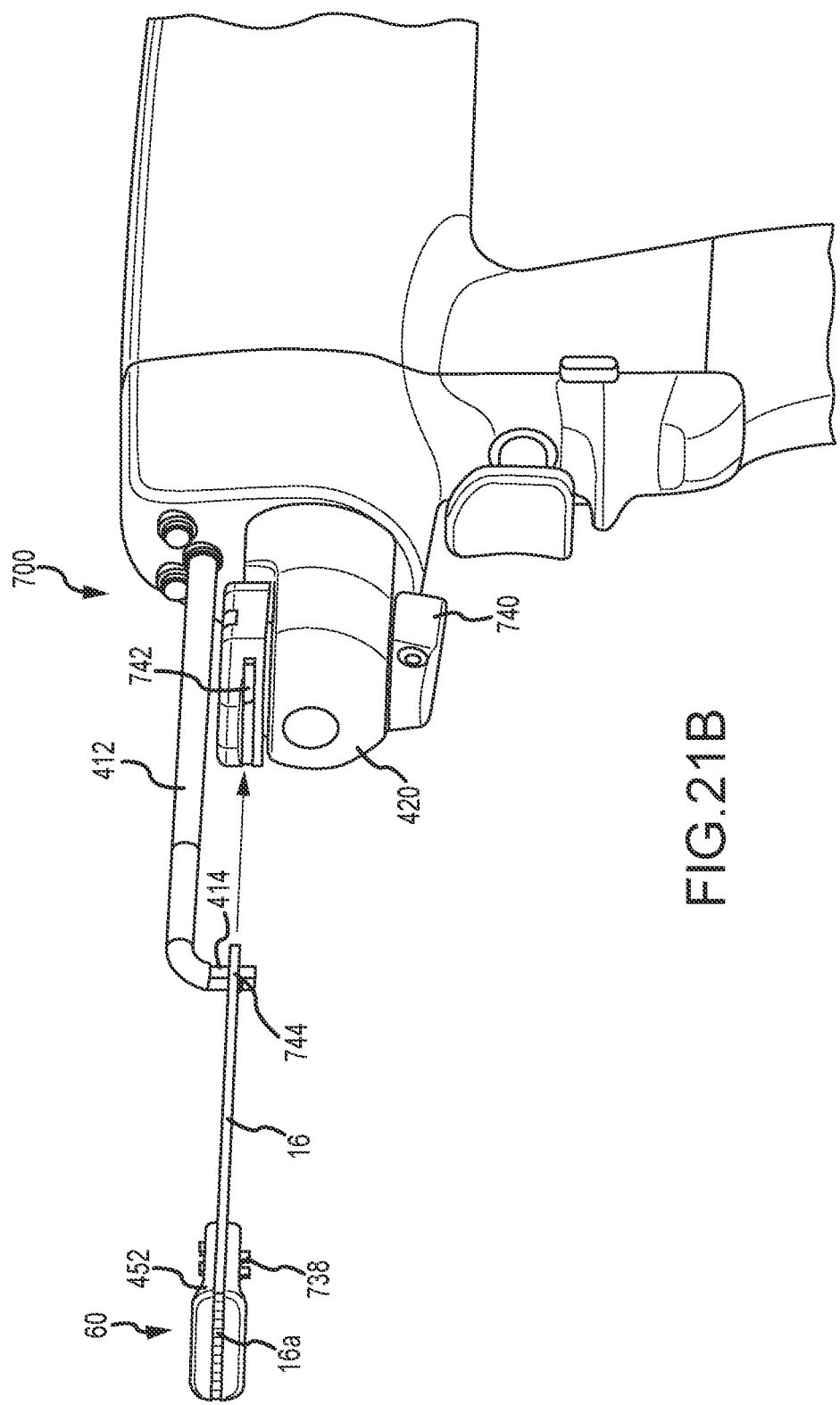

FIG. 21A depicts the chuck 420 of the saw 700 without a saw blade 16 disposed relative thereto. As may be appreciated, a lever 740 may be provided relative the chuck 420. The lever 470 may be in operative communication with a clamping element 742 disposed within a receiving window 744 of the chuck 420. In this regard, with further reference to FIG. 21B, as a saw blade assembly 60 including a bushing 452 and the saw blade 16 is advanced relative to the chuck 420, the lever 740 may be displaced, thereby displacing the clamping element 742 and allowing the shank 744 of the saw blade 16 to be received in the receiving window 7/44 the chuck 420. Upon return of the lever 742 to a home position, the clamping element 742 may clampingly engage the shank 744 of the saw blade 16. Furthermore, the engagement portion 738 of the bushing 452 may be advanced relative to the proximal end 414 of the displacement sensing arm 412 for engagement there with when the shank 744 is engaged by the chuck 420.

Furthermore, as described above, the saw blade assembly 60 for use in the embodiment of the saw 700 depicted in FIGS. 18-21C may include a destructible portion that prevents or use of the saw blade assembly 60 upon cleaning thereof. In this regard, for purposes of patient safety or the like, the saw blade assembly 60 may be a one-time use item such that attempted reuse after a cleaning operation may prevent engagement of the saw blade assembly 60 with the saw 700. Specifically, the bushing 452 may comprise a destructible portion that is destroyed upon undergoing cleaning operation and the manner described above. Specifically, the post 732 may be destroyed upon undergoing a cleaning operation such that the first portion 734 and second portion 736 may be disassociated such that there are no longer maintained within the aperture 730 of the saw blade 16.

Those skilled in the art will appreciate that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A saw blade assembly for use in a medical saw for single use applications, the saw blade assembly comprising:
    a cutting edge disposed at a distal end of a saw blade;
    a shank disposed adjacent to a proximal end of the saw blade;
    a blade member extending between the distal end and the proximal end;
    and
    a destructible portion that is at least partially destructible during a cleaning process, wherein the destructible portion is meltable.

2. The saw blade assembly according to claim 1, wherein a melting temperature of the destructible portion is greater than an operating temperature of the saw blade and less than an autoclave temperature.

3. The saw blade assembly according to claim 2, wherein the melting temperature of the destructible portion is not less than about 60° C. and not greater than about 110° C.

4. The saw blade assembly according to claim 1, wherein the destructible portion comprises a proximal end portion of the shank.

5. The saw blade assembly according to claim 4, wherein the destructible portion comprises at least a portion of an engagement feature for engagement of the shank by a chuck.

6. The saw blade assembly according to claim 5, wherein the destructible portion, after having been exposed to a cleaning process, is not registerable with respect to the chuck.

7. The saw blade assembly according to claim 1, wherein the destructible portion comprises a portion of a bushing of the saw blade assembly.

8. The saw blade assembly according to claim 7, wherein the destructible portion comprises an engagement portion of the bushing.

9. The saw blade assembly according to claim 7, wherein the destructible portion comprises a portion of the bushing constraining the bushing to the blade member, wherein upon destruction of the destructible portion, the bushing is not constrained to the blade member.

10. A method for a tool assembly for use in an instrument for single use applications, comprising:
   exposing a tool of the tool assembly to a cleaning process; and
   degrading at least a portion of a destructible portion of the tool assembly in response to the exposing, wherein the degrading comprises melting at least a portion of the destructible portion.

11. The method according to claim 10, wherein the tool comprises a saw blade and wherein exposing comprises autoclaving the saw blade.

12. The method according to claim 11, wherein the degrading comprises melting at least the portion of the destructible portion in response to the autoclaving.

13. The method according to claim 12, wherein the melting occurs at a temperature of not less than about 60° C. and not greater than about 110° C.

14. The method according to claim 10, wherein the exposing comprises applying a cleaning chemical to the tool assembly and the degrading comprises removing of at least a portion of the destructible portion in response to applying the cleaning chemical.

15. The method according to claim 10, wherein the tool comprises a saw blade and the degrading results in changing a shape of a shank of the saw blade.

16. The method according to claim 15, wherein the degrading comprises removing at least a portion of the destructible portion at a shank of the saw blade.

17. The method according to claim 16, wherein the portion of the destructible portion removed comprises at least a portion of an engagement feature for engagement of the shank by a chuck.

18. The method according to claim 12, wherein the degrading results in reducing a registration of the shank with respect to a chuck of a saw.

19. The method according to claim 10 wherein the tool comprises a saw blade and wherein the degrading comprises removing at least a portion of the destructible portion at a bushing.

20. The method according to claim 19, wherein the degrading comprises destroying an engagement portion of the bushing.

21. The method according to claim 20, wherein the degrading comprises destroying a portion of the bushing constraining the bushing to a blade member, wherein upon the destroying of the destructible portion, the bushing is not constrained to the blade member.

22. A tool including a tool portion penetration measuring system for determining, with respect to a reference point, a depth of penetration of an edge of the tool portion, the tool comprising:
   a chuck for engagement with a shank of the tool portion, wherein the chuck is operable to constrain the tool portion engaged by the chuck to limit relative axial movement relative to an operating direction of the tool portion;
   a displacement sensing arm extending from the tool, wherein the displacement sensing arm is engageable with a bushing member that is constrainedly moveable relative to the tool portion along the operating direction of the tool portion when the tool portion is engaged by the chuck; and
   a displacement sensor disposed in a fixed relative position with respect to the tool portion engaged by the chuck at least in a direction corresponding to a length of the tool portion, the displacement sensing arm being adapted for relative movement with respect to the displacement sensor, wherein the displacement sensor is operative to output a first signal representative of the displacement of the displacement sensing arm relative to the displacement sensor;
   wherein the movement of the displacement sensing arm relative to the tool corresponds to displacement of the bushing relative to the tool portion engaged by the chuck.

23. The tool according to claim 22, wherein the displacement sensor is disposed internally to a tool housing and the displacement sensing arm extends from the tool housing.

* * * * *